US012590085B2

(12) United States Patent
Hyun et al.

(10) Patent No.: US 12,590,085 B2
(45) Date of Patent: Mar. 31, 2026

(54) ORGANIC LIGHT EMITTING COMPOUND AND ORGANIC LIGHT EMITTING DEVICE INCLUDING SAME

(71) Applicant: P&H TECH Co., Ltd., Yongin-si (KR)

(72) Inventors: Seo-Yong Hyun, Gyeonggi-do (KR); Seok-Keun Yoon, Gyeonggi-do (KR)

(73) Assignee: P&H TECH CO., LTD., Gyeonggi-Do (KR)

( * ) Notice: Subject to any disclaimer, the term of this patent is extended or adjusted under 35 U.S.C. 154(b) by 881 days.

(21) Appl. No.: 17/909,255

(22) PCT Filed: Oct. 20, 2020

(86) PCT No.: PCT/KR2020/014294

§ 371 (c)(1),
(2) Date: Sep. 2, 2022

(87) PCT Pub. No.: WO2021/182704

PCT Pub. Date: Sep. 16, 2021

(65) Prior Publication Data

US 2023/0150992 A1 May 18, 2023

(30) Foreign Application Priority Data

Mar. 12, 2020 (KR) ........................ 10-2020-0030765

(51) Int. Cl.

| | |
|---|---|
| ***C07D 413/14*** | (2006.01) |
| ***C07D 519/00*** | (2006.01) |
| ***H10K 85/60*** | (2023.01) |
| *B82Y 30/00* | (2011.01) |
| *H10K 102/00* | (2023.01) |

(52) U.S. Cl.

CPC ......... *C07D 413/14* (2013.01); *C07D 519/00* (2013.01); *H10K 85/652* (2023.02); *H10K 85/654* (2023.02); *H10K 85/657* (2023.02); *H10K 85/6572* (2023.02); *B82Y 30/00* (2013.01); *H10K 2102/351* (2023.02)

(58) Field of Classification Search

None

See application file for complete search history.

(56) References Cited

U.S. PATENT DOCUMENTS

2003/0129448 A1 7/2003 Lin et al.

FOREIGN PATENT DOCUMENTS

| | | | |
|---|---|---|---|
| CN | 105418485 | A | 3/2016 |
| KR | 1020170116927 | A | 10/2017 |
| KR | 1020200005489 | A | 1/2020 |
| KR | 1020200022963 | A | 3/2020 |

OTHER PUBLICATIONS

Machine English translation of Seo et al. (KR 10-2020-0022963). Sep. 17, 2025.*

PCT International Search Report and Written Opinion; International Application No. PCT/KR2020/014294; International Filing Date Oct. 10, 2020; 8 pages.

* cited by examiner

*Primary Examiner* — Jay Yang

(74) *Attorney, Agent, or Firm* — Umberg Zipser LLP

(57) ABSTRACT

The present invention relates to an organic light emitting compound that is employed for a light efficiency improving layer provided in an organic light emitting device. The organic light emitting device employing the same achieves low-voltage driving of a further improved device and excellent luminous efficiency through improved light extraction efficiency, and thus can be usefully used in various display devices.

8 Claims, 1 Drawing Sheet

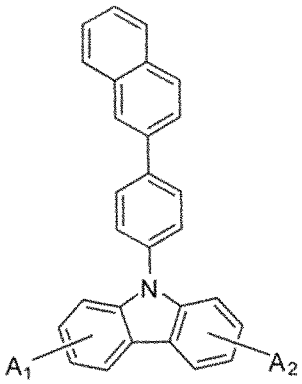

ORGANIC LIGHT EMITTING COMPOUND AND ORGANIC LIGHT EMITTING DEVICE INCLUDING SAME

TECHNICAL FIELD

The present invention relates to an organic light emitting compound, and more particularly, to an organic light emitting compound that is employed as a material for a light efficiency improving layer (capping layer) provided in an organic light emitting device, and an organic light emitting device that employs the same, thus achieving greatly improved luminescent properties such as low-voltage driving of the device and excellent luminous efficiency.

BACKGROUND ART

The organic light emitting device may be formed even on a transparent substrate, and may be driven at a low voltage of 10 V or less compared to a plasma display panel or an inorganic electroluminescence (EL) display. In addition, the device consumes relatively little power and has good color representation. The device may display three colors of green, blue, and read, and thus has recently become a subject of intense interest as a next-generation display device.

However, in order for such an organic light emitting device to exhibit the aforementioned characteristics, the materials constituting an organic layer in the device, such as hole injecting materials, hole transport materials, light emitting materials, electron transport materials, and electron injecting materials, are prerequisites for the support by stable and efficient materials. However, the development of a stable and efficient organic layer material for an organic light emitting device has not yet been sufficiently made.

Thus, further improvements in terms of efficiency and life characteristics are required for good stability, high efficiency, long lifetime, and large size of organic light emitting devices. Particularly, there is a strong need to develop materials constituting each organic layer of organic light emitting devices.

In this connection, recently, with respect to the materials of hole transport layers in the structure of organic light emitting devices, research for improving the conductivity (mobility) of the existing organic materials has been actively conducted.

In addition, recently, research aimed at improving the characteristics of organic light emitting devices by changes in the performance of each organic layer material, as well as a technique for improving the color purity and enhancing the luminous efficiency by optimizing the optical thickness between an anode and a cathode are considered as one of the crucial factors for improving the device performance. As an example of this method, an increase in light efficiency and excellent color purity are achieved by using a capping layer on an electrode.

DISCLOSURE

Technical Problem

An aspect of the present invention intends to provide a novel organic light emitting compound that is employed as a light efficiency improving layer provided in an organic light emitting device, achieving excellent luminescent properties such as low-voltage driving of the device and improved luminous efficiency, and an organic light emitting device including the same.

Technical Solution

An aspect of the present invention provides any one organic light emitting compound selected from the compounds represented by Formula I below:

[Formula I]

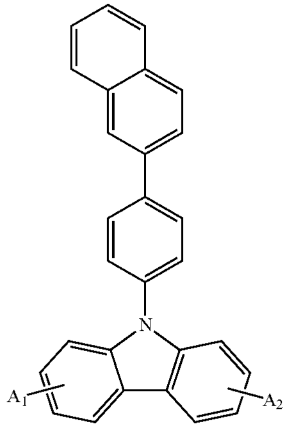

Characteristic structures of Formula I above and $A_1$ to $A_2$ will be described later.

In addition, an aspect of the present invention provides an organic light emitting device including a first electrode, a second electrode, and one or more organic layers arranged between the first and second electrodes, wherein the organic light emitting device further includes a light efficiency improving layer (capping layer) formed on at least one side opposite to the organic layer among the upper or lower portions of the first electrode and the second electrode, and the light efficiency improving layer includes an organic light emitting compound represented by Formula I above.

According to an embodiment of the present invention, the light efficiency improving layer has a thickness of 50 to 150 nm, and has a refractive index value of 2.10 or more at a wavelength of 450 nm.

Advantageous Effects

When an organic light emitting compound according to an embodiment of the present invention is employed as a material for a light efficiency improving layer provided in an organic light emitting device, it is possible to achieve luminescent properties such as low-voltage driving of the device and excellent luminous efficiency, and thus can be usefully used in various display devices.

DESCRIPTION OF DRAWINGS

FIG. 1 is a representative view showing the structure of an organic light emitting compound according to an embodiment of the present invention.

BEST MODE

Hereinafter, the present invention will be described in more detail.

An embodiment of the present invention relates to an organic light emitting compound represented by Formula I below that is employed as a light efficiency improving layer provided in an organic light emitting device, achieving luminescent properties such as low-voltage driving of the device and excellent luminous efficiency:

[Formula I]

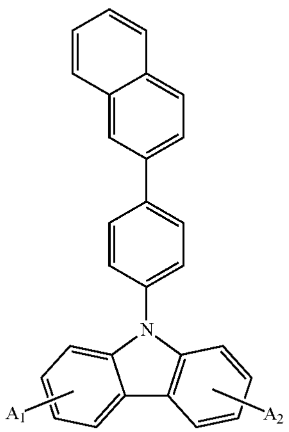

In Formula I above, $A_1$ to $A_2$ are the same as or different from each other, and are each independently represented by Structural Formula 1 below.

As such, the compound according to an embodiment of the present invention is characterized in that Structural Formula 1 below is introduced into the skeletal structure structurally represented by Formula I, thus achieving an organic light emitting device that employs a material suitable for a light efficiency improving layer and has luminescent properties such as low-voltage driving and excellent efficiency:

[Structural Formula 1]

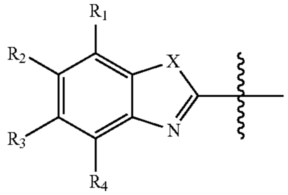

In Structural Formula 1 above, X is O or S.

$R_1$ to $R_4$ are the same as or different from each other, and are each independently selected from hydrogen, deuterium, a halogen group, a cyano group, a substituted or unsubstituted C1 to C20 alkyl group, a substituted or unsubstituted C2 to C20 alkenyl group, a substituted or unsubstituted C3 to C20 cycloalkyl group, a substituted or unsubstituted C1 to C20 alkoxy group, a substituted or unsubstituted C1 to C20 halogenated alkyl group, a substituted or unsubstituted C1 to C20 halogenated alkoxy group, a substituted or unsubstituted C6 to C30 aryl group, and a substituted or unsubstituted C3 to C30 heteroaryl group.

The $R_1$ to $R_4$ may be bonded to each other or linked to adjacent substituents to form at least one alicyclic or aromatic monocyclic or polycyclic ring whose carbon atoms may be substituted with one or more heteroatoms selected from nitrogen (N), sulfur (S), and oxygen (O) atoms.

Accordingly, Structural Formula 1 above may be any one selected from among those represented by Structural Formula 2 to Structural Formula 6 below:

[Structural Formula 2]

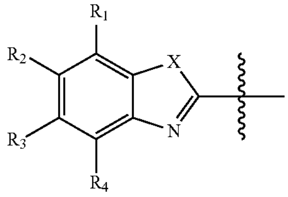

[Structural Formula 3]

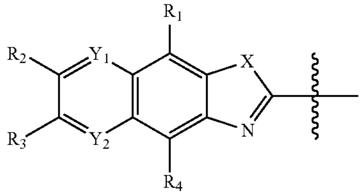

[Structural Formula 4]

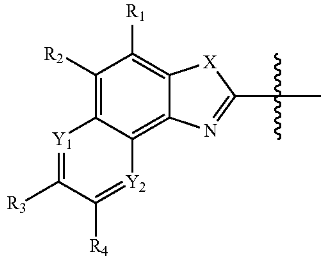

[Structural Formula 5]

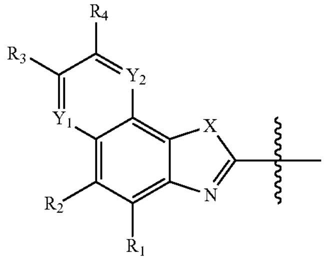

[Structural Formula 6]

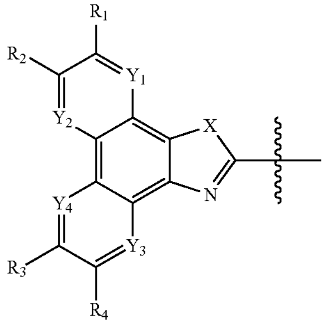

In Structural Formula 2 to Structural Formula 6 above, X is O or S.

$Y_1$ to $Y_4$ are the same as or different from each other, and each independently represents N or $CR_5$.

$R_1$ to $R_4$ and the $R_5$ are the same as or different from each other, and are each independently selected from hydrogen, deuterium, a halogen group, a cyano group, a substituted or unsubstituted C1 to C20 alkyl group, a substituted or unsubstituted C2 to C20 alkenyl group, a substituted or unsubstituted C3 to C20 cycloalkyl group, a substituted or unsubstituted C1 to C20 alkoxy group, a substituted or unsubstituted C1 to C20 halogenated alkyl group, a substituted or unsubstituted C1 to C20 halogenated alkoxy group, a substituted or unsubstituted C6 to C30 aryl group, and a substituted or unsubstituted C3 to C30 heteroaryl group.

The term "substituted" or "unsubstituted" in the definition of $R_1$ to $R_5$ above indicates substitution with one or more substituents selected from the group consisting of hydrogen, deuterium, a halogen group, a cyano group, a nitro group, a hydroxyl group, a silyl group, an alkyl group, a cycloalkyl group, an alkoxy group, an alkenyl group, an aryl group, and a heterocyclic group, substitution with a substituent to which two or more of the substituents are linked, or having no substituent.

For specific examples, the substituted arylene group means that a phenyl group, a biphenyl group, a naphthalene group, a fluorenyl group, a pyrenyl group, a phenanthrenyl group, a perylene group, a tetracenyl group, and an anthracenyl group are substituted with other substituents.

In addition, the substituted heteroarylene group means that a pyridyl group, a thiophenyl group, a triazine group, a quinoline group, a phenanthroline group, an imidazole group, a thiazole group, an oxazole group, a carbazole group and a condensate heteroring group thereof, for example, a benzquinoline group, a benzimidazole group, a benzoxazole group, a benzthiazole group, a benzcarbazole group, a dibenzothiophenyl group, and a dibenzofuran group are substituted with other substituents.

In an embodiment of the present invention, examples of the substituents will be described in detail below, but are not limited thereto.

In an embodiment of the present invention, the alkyl groups may be straight or branched. The number of carbon atoms in the alkyl groups is not particularly limited but is preferably from 1 to 20. Specific examples of the alkyl groups include, but are not limited to, methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 2-methylpentyl, 4-methylhexyl, and 5-methylhexyl groups.

In an embodiment of the present invention, the alkoxy groups may be straight or branched. The number of carbon atoms in the alkoxy groups is not particularly limited but is preferably from 1 to 20 as long as steric hindrance is avoided. Specific examples of the alkoxy groups include, but are not limited to, methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, and p-methylbenzyloxy groups.

In an embodiment of the present invention, the aryl groups may be monocyclic or polycyclic. The number of carbon atoms in the aryl groups is not particularly limited but is preferably from 6 to 30. Examples of the monocyclic aryl groups include phenyl, biphenyl, terphenyl, and stilbene groups but the scope of the present invention is not limited thereto. Examples of the polycyclic aryl groups include naphthyl, anthracenyl, phenanthrenyl, pyrenyl, perylenyl, tetracenyl, chrysenyl, fluorenyl, acenaphathcenyl, triphenylene, and fluoranthrene groups, but the scope of the present invention is not limited thereto.

In addition, in an embodiment of the present invention, the fluorenyl groups refer to structures in which two cyclic organic compounds are linked through one atom, and examples thereof include and

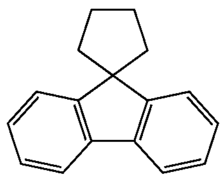

and

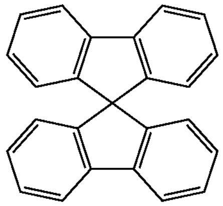

.

In an embodiment of the present invention, the fluorenyl groups include open structures in which one of the two cyclic organic compounds linked through one atom is cleaved, and examples thereof include

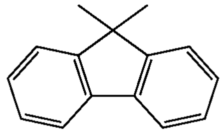

and

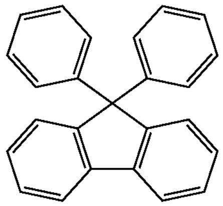

.

In an embodiment of the present invention, the heteroaryl groups refer to heterocyclic groups containing heteroatoms selected from O, N, and S. The number of carbon atoms is not particularly limited, but preferably from 2 to 30. In an embodiment of the present invention, specific examples thereof include, but are not limited to, thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phthalazinyl, pyridopyrimidinyl, pyridopyrazinyl, pyrazinopyrazinyl, isoquinoline, indole, carbazole, benzoxazole, benzimidazole, benzothiazole, benzocarbazole, benzothiophene, dibenzothiophene, benzofuranyl, dibenzofuranyl, phenanthroline, thiazolyl, isoxazolyl, oxadiazolyl, thiadiazolyl, benzothiazolyl, phenothiazinyl, phenoxazine, and phenothiazine groups.

In an embodiment of the present invention, specific examples of the silyl groups include, but are not limited to, trimethylsilyl, triethylsilyl, t-butyldimethylsilyl, vinyldimethylsilyl, propyldimethylsilyl, triphenylsilyl, diphenylsilyl, and phenylsilyl groups.

Specific examples of the halogen groups as substituents used in an embodiment of the present invention include fluorine (F), chlorine (Cl), and bromine (Br).

The organic light emitting compound according to an embodiment of the present invention represented by Formula I above may be used to form various organic layers of an organic light emitting device due to its structural features. More specifically, the organic light emitting compound may be used as a material for a light emitting layer, a hole transport layer, or a light efficiency improving layer in an organic layer.

Preferred and specific examples of the organic light emitting compound represented by Formula I according to an embodiment of the present invention include the following compounds, but are not limited thereto:

1
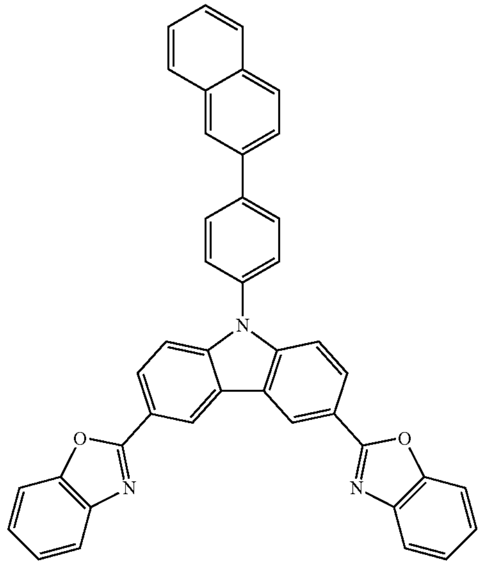
2
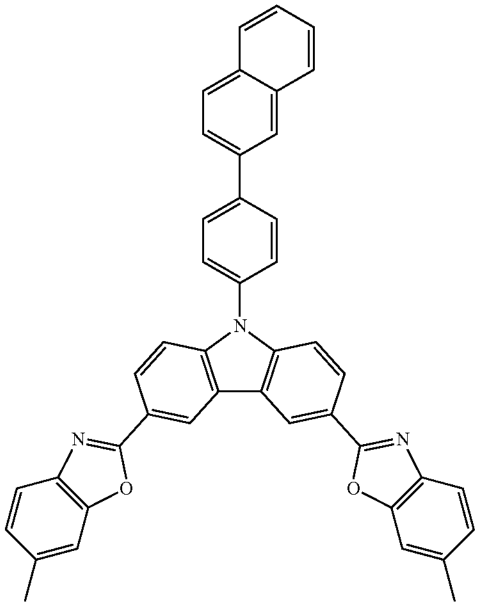
3
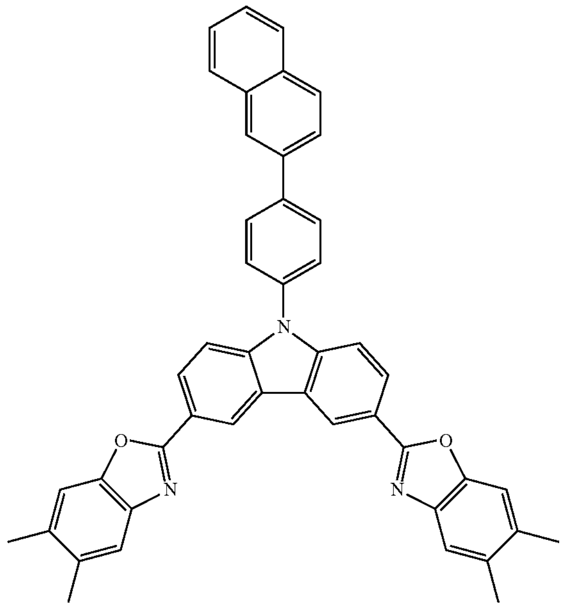
4
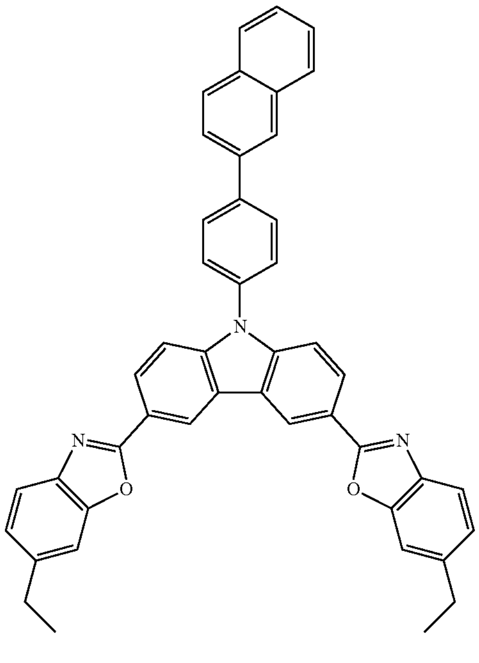

-continued
5
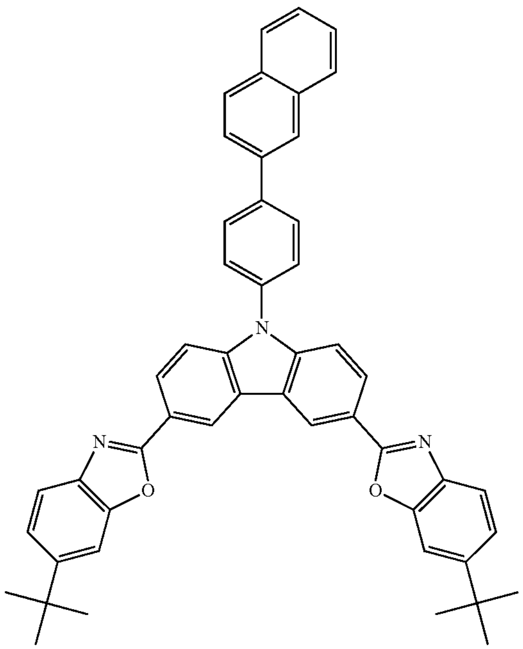
6
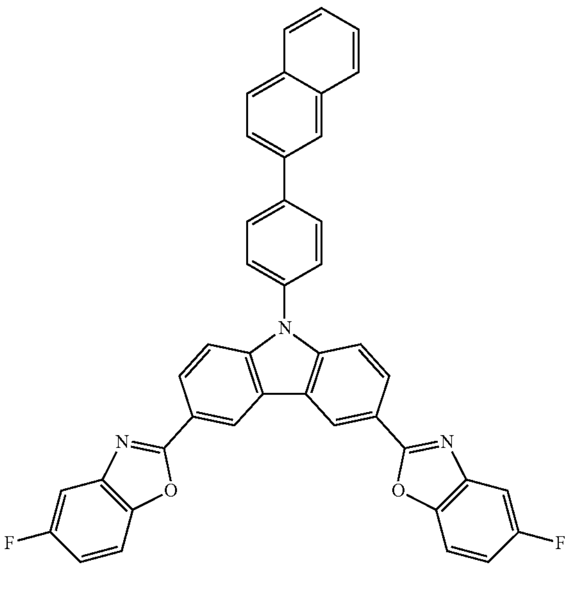
7
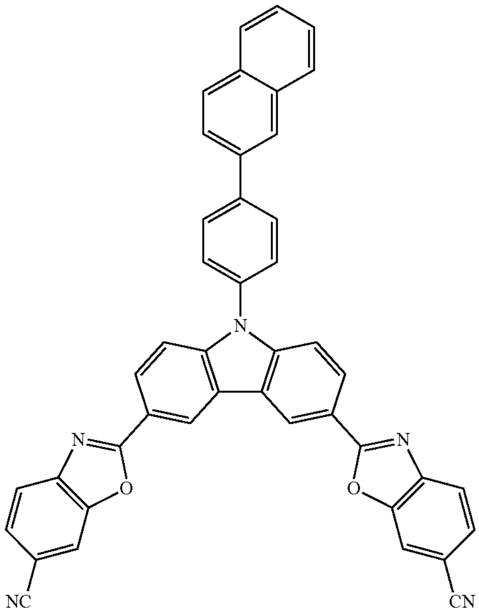
8
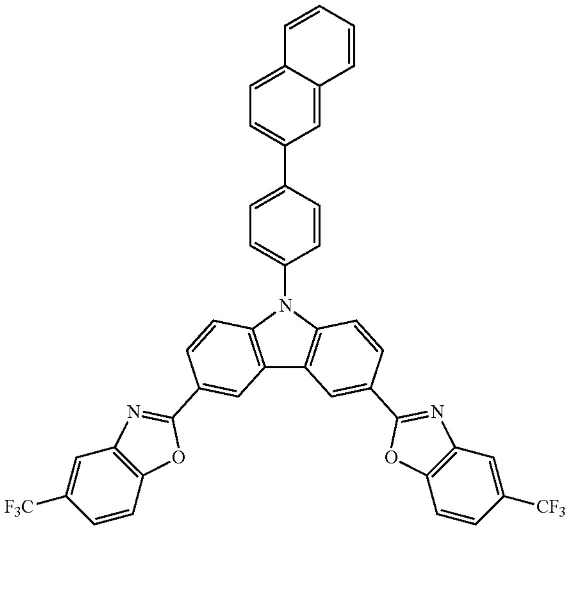

-continued
9
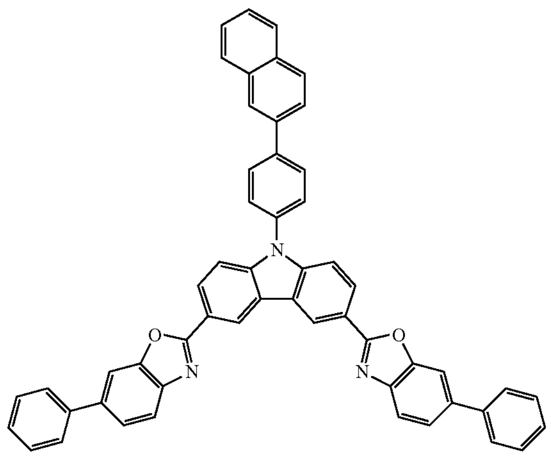
10
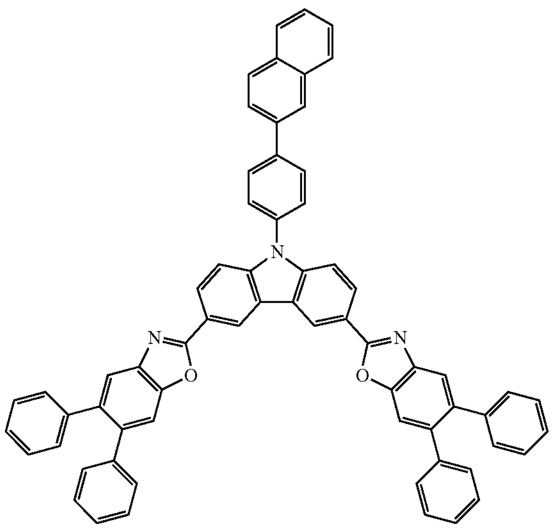
11
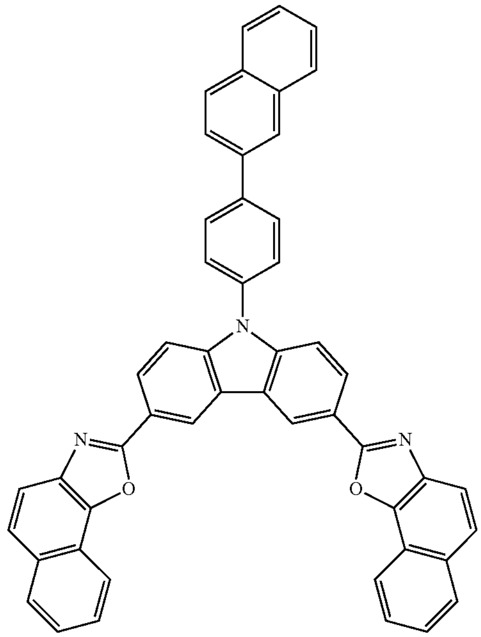
12
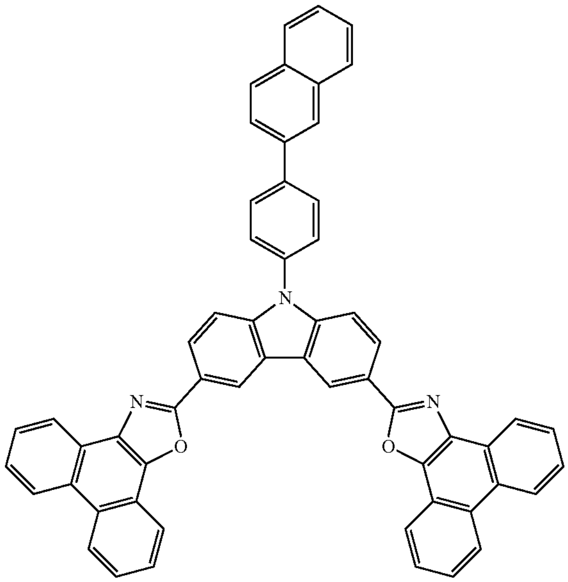

-continued
13
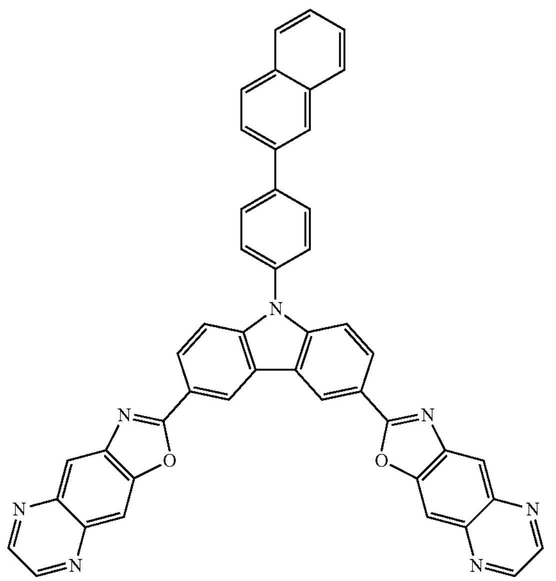
14
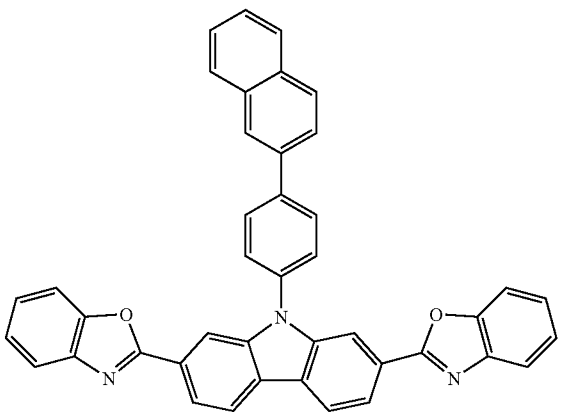
15
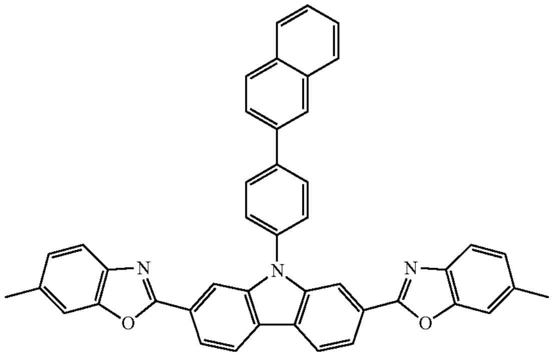
16
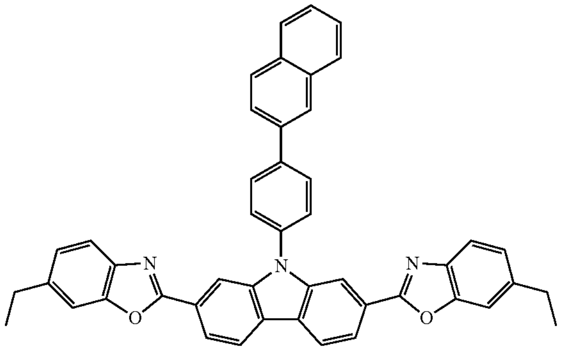
17
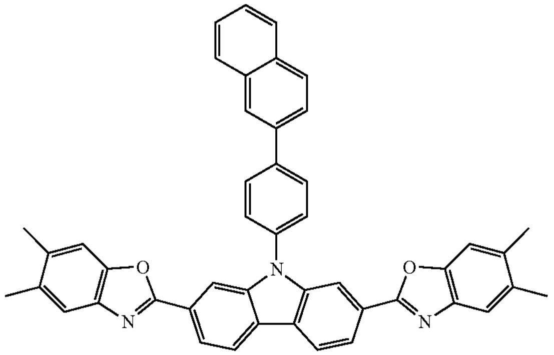
18
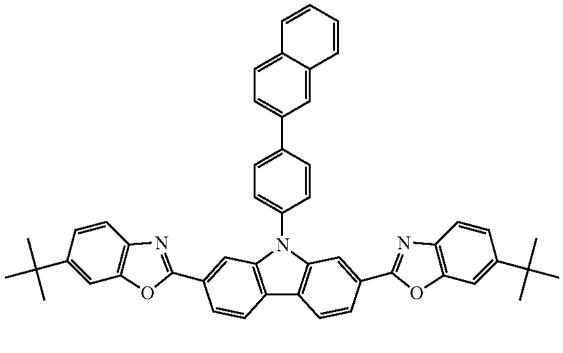

-continued
19
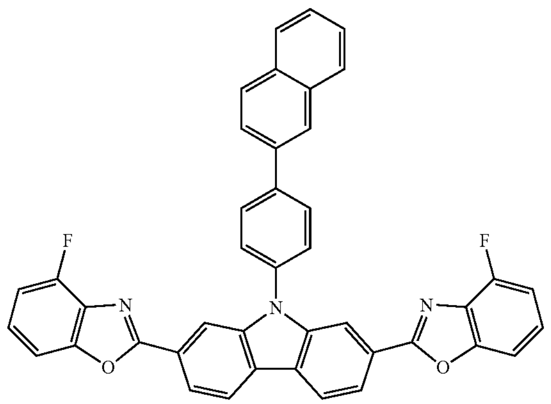
20
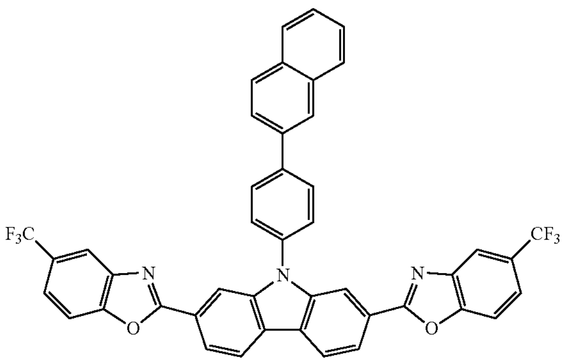
21
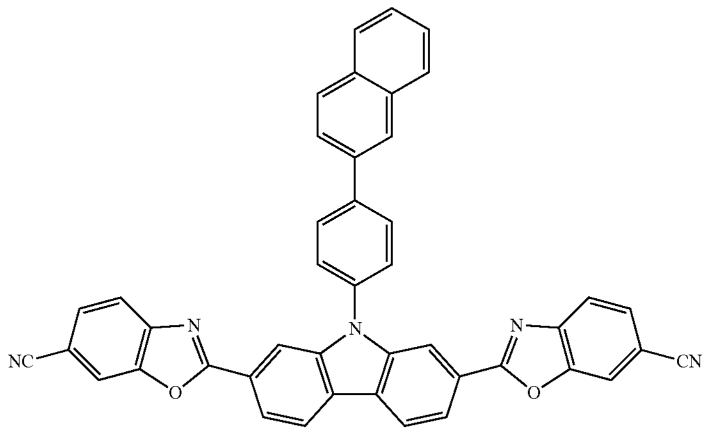
22
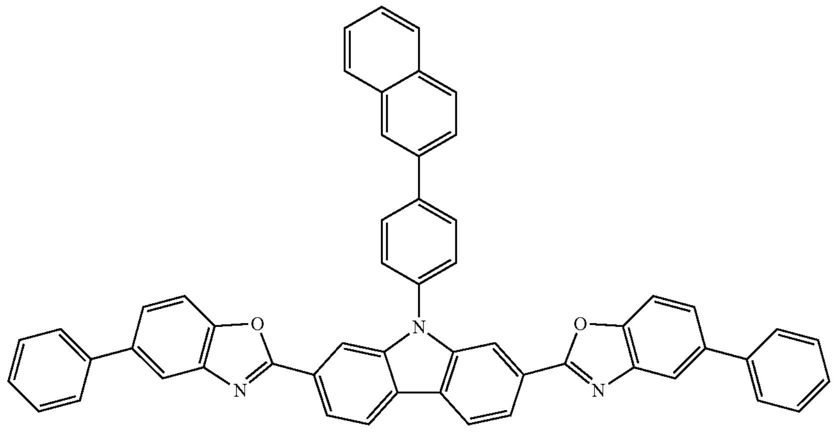

-continued
23
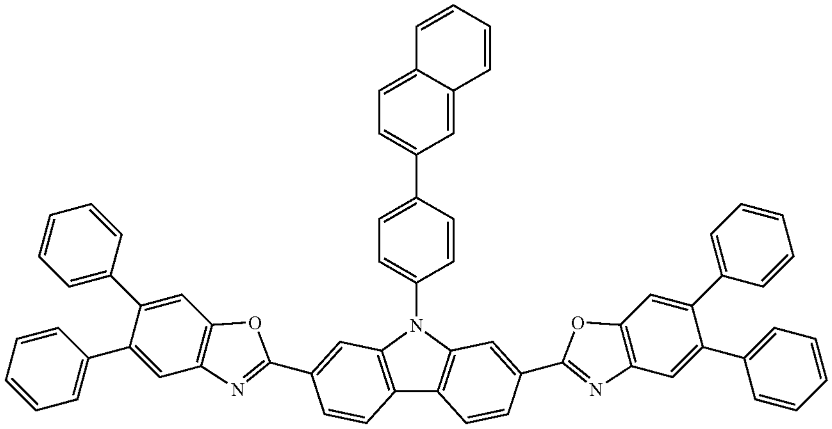
24
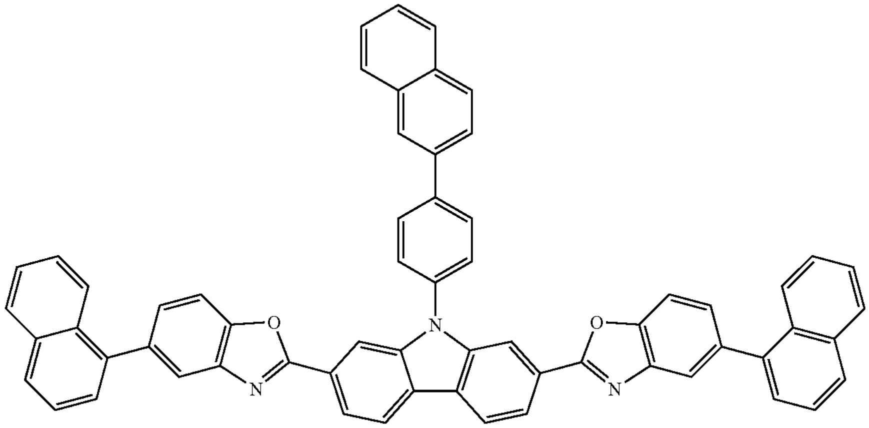
25
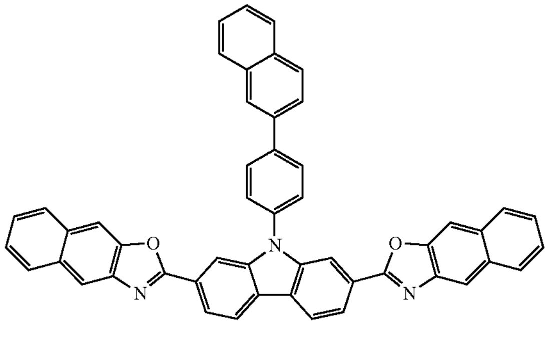
26
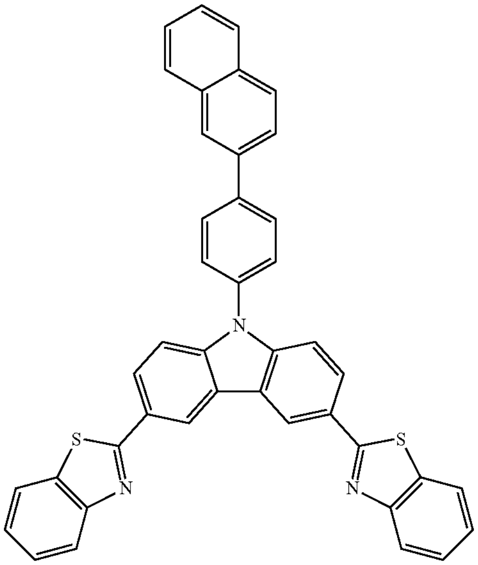

-continued
27
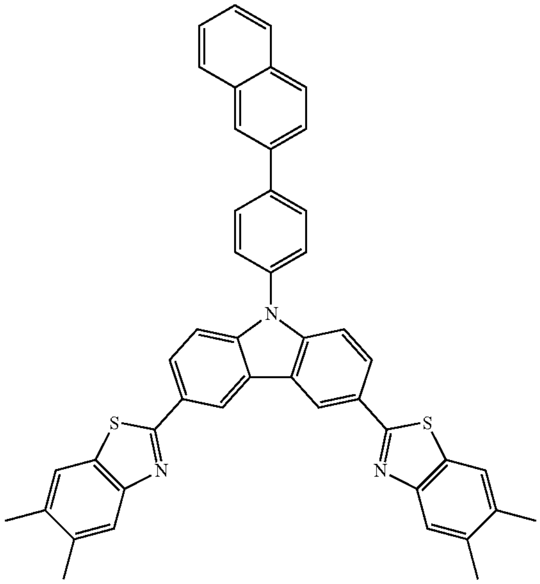
28
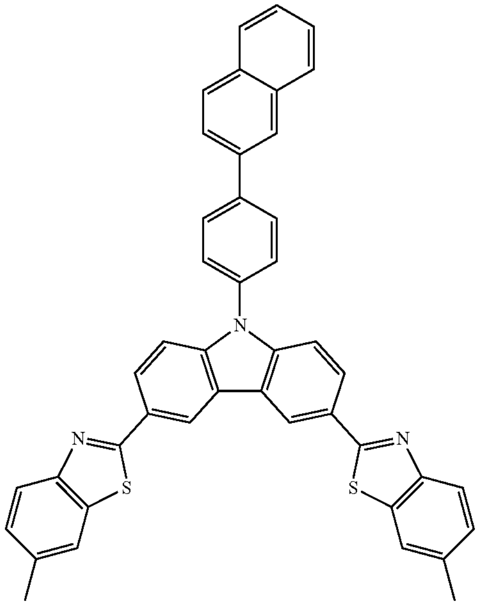
29
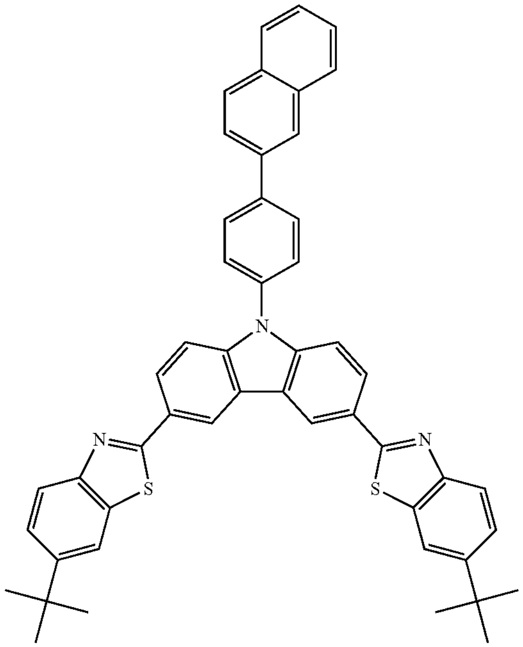
30
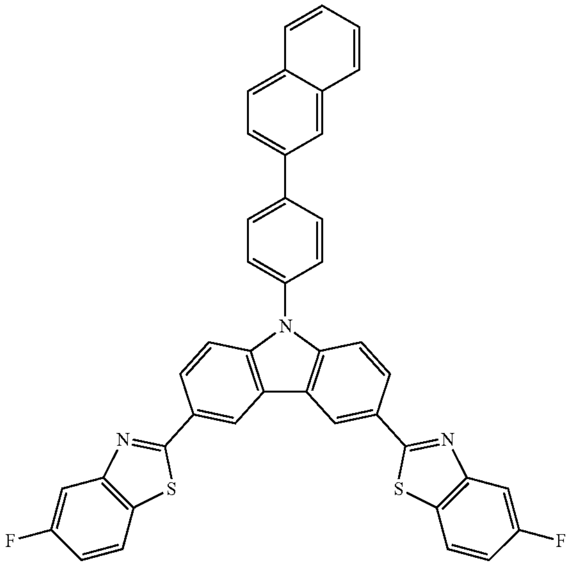

-continued
31
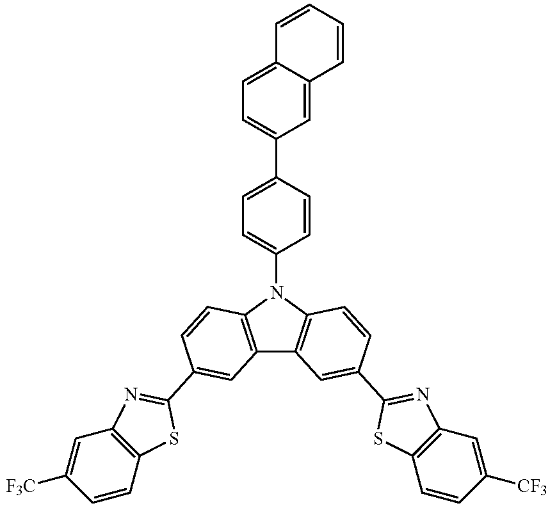
32
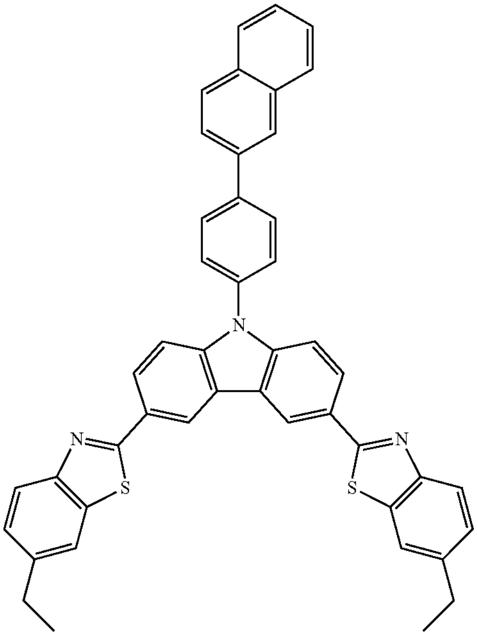
33
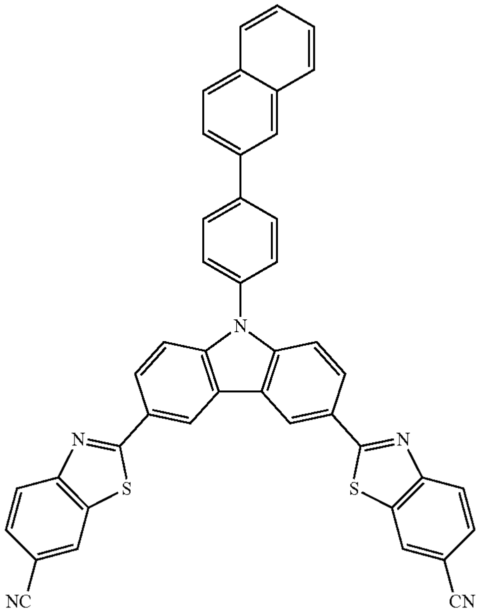
34
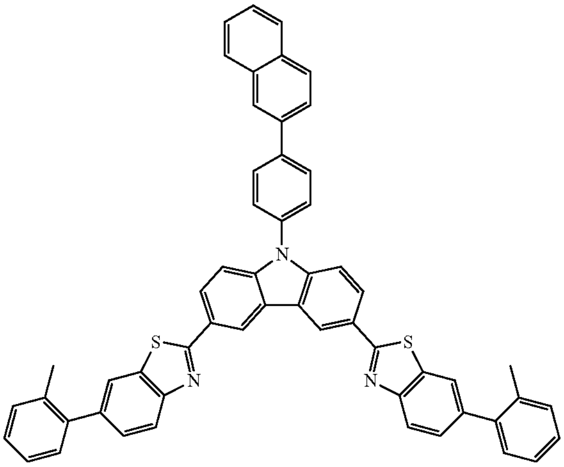

-continued
35
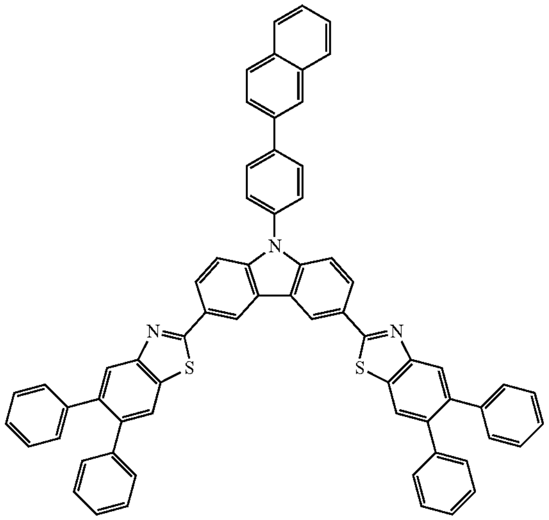
36
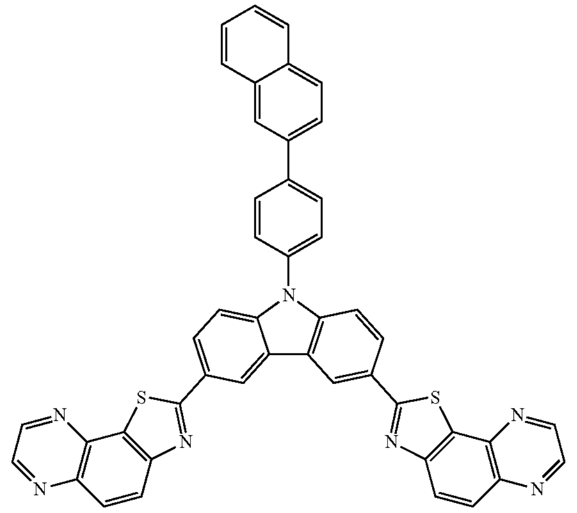
37
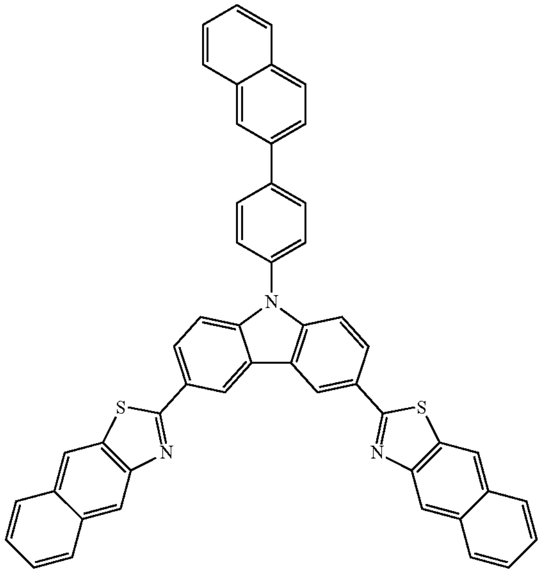
38
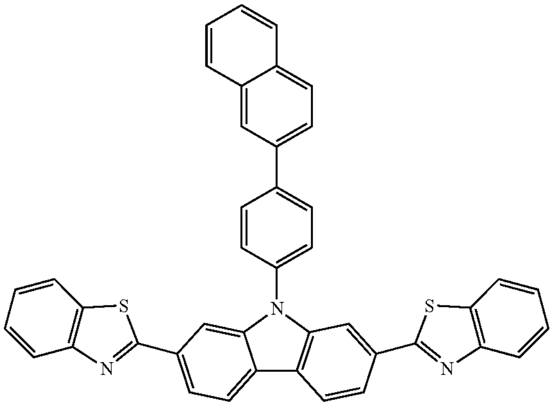
39
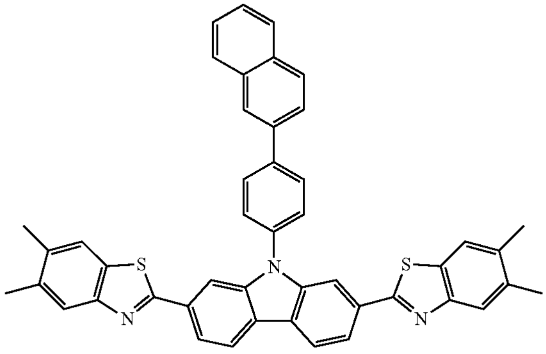
40
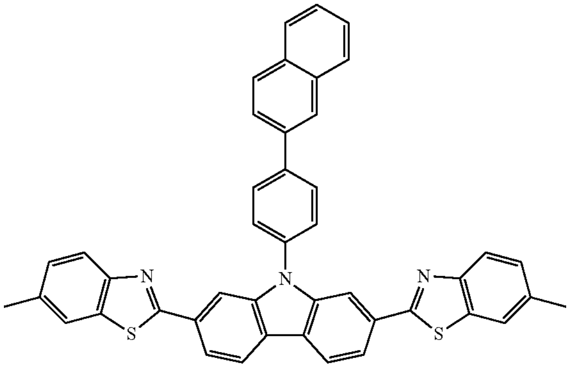

-continued
41
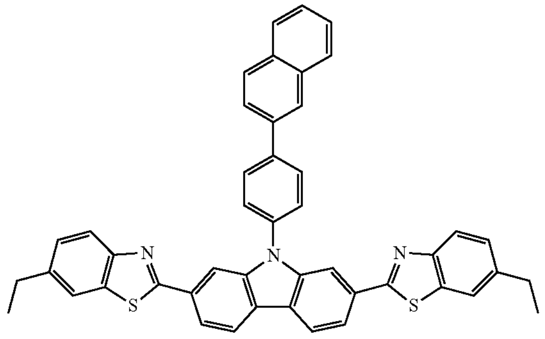
42
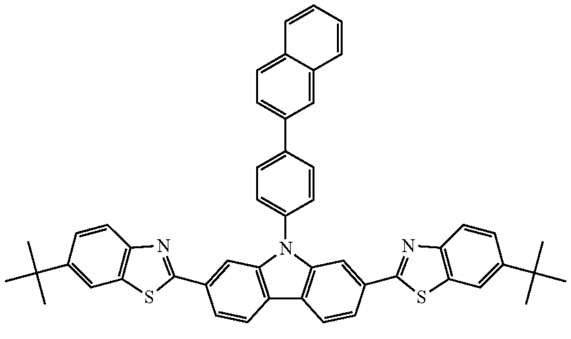
43
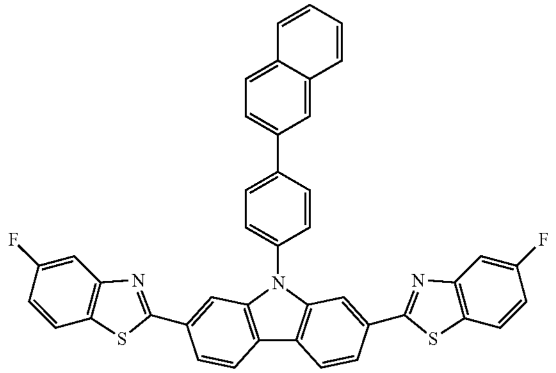
44
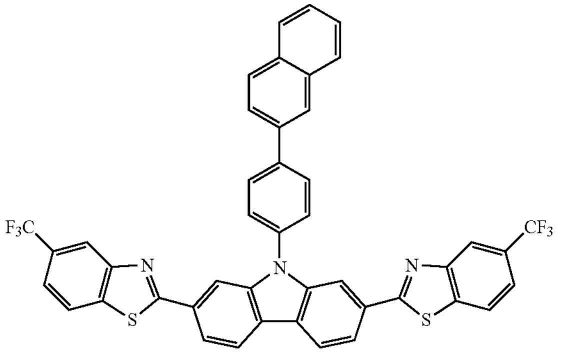
45
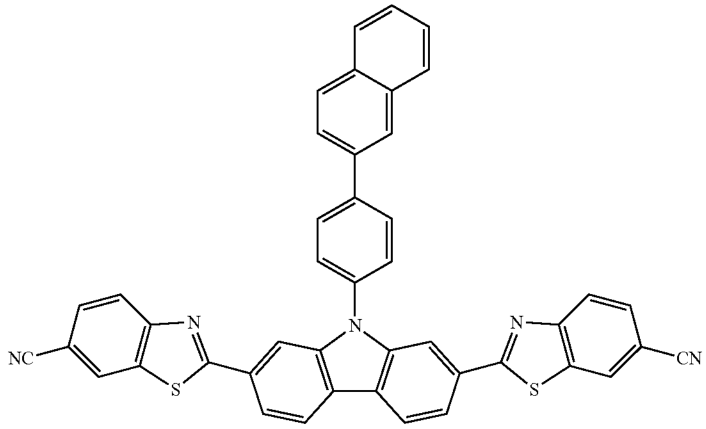
46
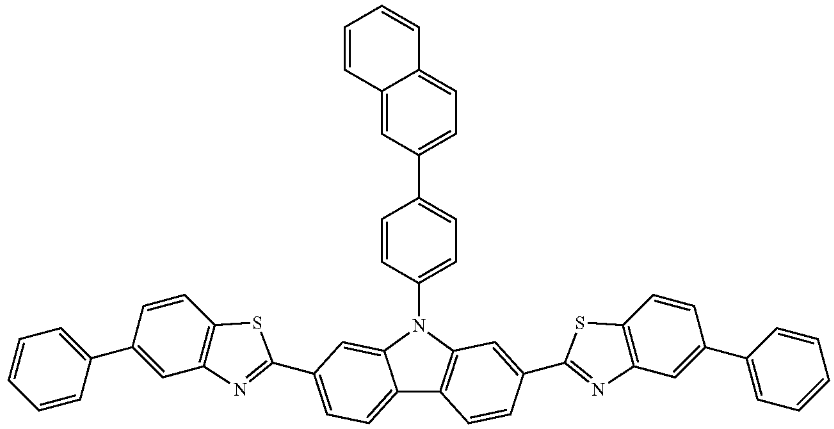

-continued
47
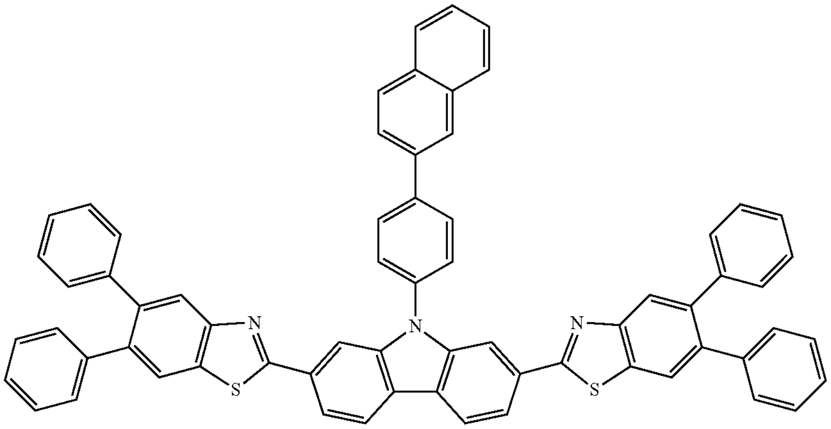
48
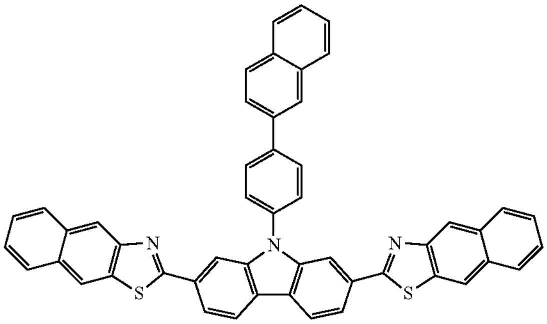
49
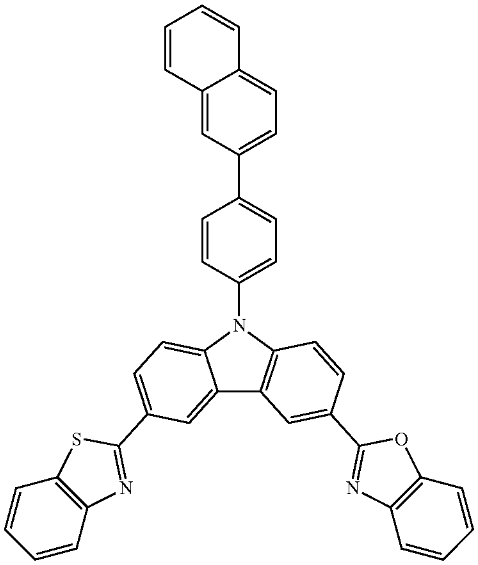
50
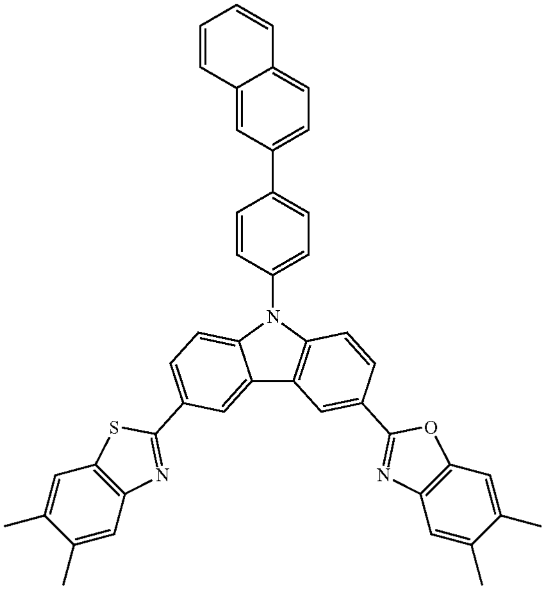
51
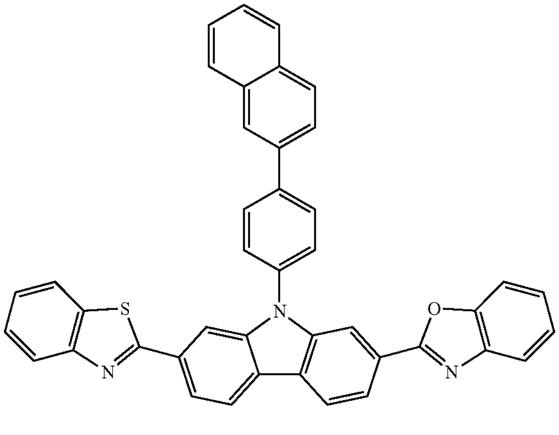

-continued

52

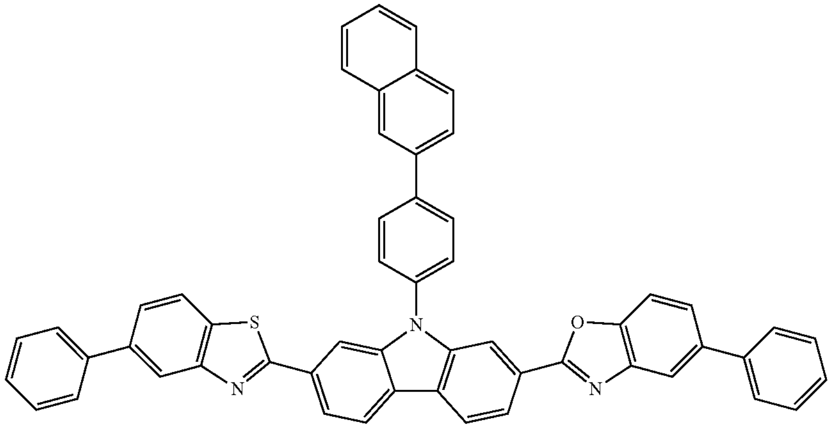

53

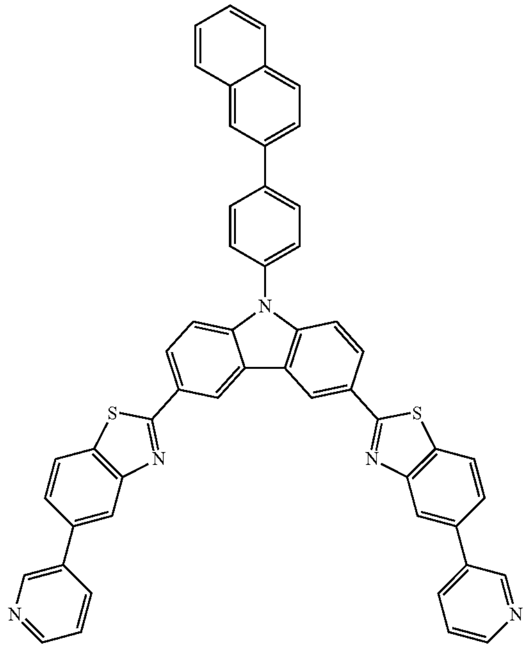

54

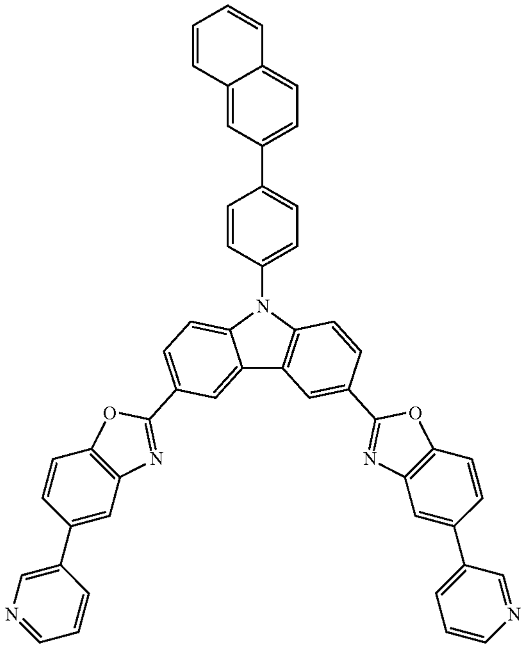

55

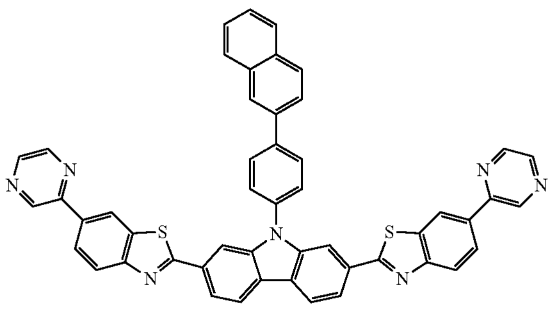

56

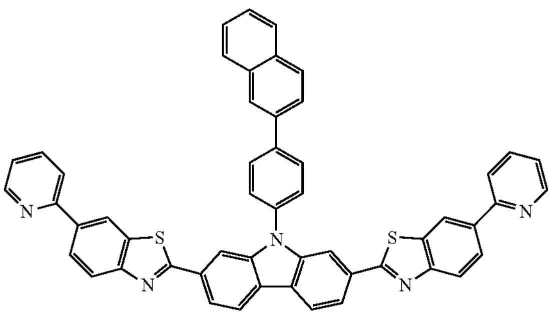

As such, the organic light emitting compound of an embodiment of the present invention exhibits inherent characteristics due to its characteristic skeleton and has various characteristics due to the inherent characteristics of the moieties introduced into the skeleton. As a result, the organic light emitting compound of an embodiment of the present invention may be employed as a material for various organic layers of an organic light emitting device such as a light emitting layer, a capping layer, a hole transport layer, an electron transport layer and/or an electron blocking layer, achieving further improved luminescent properties (including high luminous efficiency) of the device.

In addition, the compound of an embodiment of the present invention may be applied to a device according to a general method for manufacturing an organic light emitting device.

An organic light emitting device according to an embodiment of the present invention may include a first electrode, a second electrode, and an organic layer arranged therebetween. The organic light emitting device may be manufactured using a general device manufacturing method and material, except that the organic light emitting compound of an embodiment of the present invention is used to form the organic layer of the device.

The organic layer of the organic light emitting device according to an embodiment of the present invention may have a monolayer structure or a multilayer structure in which two or more organic layers are stacked. For example, the structure of the organic layers may include a hole injecting layer, a hole transport layer, a light emitting layer, an electron transport layer, an electron injecting layer, an electron blocking layer, a hole blocking layer, and a light efficiency improving layer (capping layer). The number of the organic layers is not limited and may be increased or decreased.

In addition, the organic electroluminescent device may include a substrate, a first electrode (anode), an organic layer, a second electrode (cathode), and a light efficiency improving layer (capping layer), of which may be formed under the first electrode (bottom emission type) or on the second electrode (top emission type).

When the organic electroluminescent device is of a top emission type, light from the light emitting layer is emitted to the cathode and passes through the light efficiency improving layer (CPL) formed using the compound according to an embodiment of the present invention having a relatively high refractive index. The wavelength of the light is amplified, resulting in an increase in luminous efficiency. When the organic electroluminescent device is of a bottom emission type, the compound according to an embodiment of the present invention is employed in the light efficiency improving layer to improve the luminous efficiency of the organic electroluminescent device based on the same principle.

Preferred structures of the organic layers of the organic light emitting according to an embodiment of the present invention will be explained in more detail in the examples to be described later.

In addition, the organic electroluminescent device of an embodiment of the present invention may be manufactured by depositing a metal, a conductive metal oxide or an alloy thereof on a substrate by a physical vapor deposition (PVD) method such as sputtering or e-beam evaporation to form an anode, forming organic layers including a hole injecting layer, a hole transport layer, a light emitting layer, and an electron transport layer thereon, and depositing a cathode material thereon.

In addition to the above methods, the organic light emitting device may be fabricated by depositing a cathode material, organic layer materials, and an anode material in this order on a substrate. The organic layers may have a multilayer structure including a hole injecting layer, a hole transport layer, a light emitting layer, and an electron transport layer, but is not limited thereto and may have a monolayer structure. In addition, the organic layers may be manufactured in a smaller number of layers by a solvent process using various polymer materials rather than by a deposition process, such as spin coating, dip coating, doctor blading, screen printing, inkjet printing or thermal transfer.

As the anode material, a material having a high work function is generally preferred for easy injection of holes into the organic layers. Specific examples of anode materials suitable for use in an embodiment of the present invention include, but are not limited to: metals such as vanadium, chromium, copper, zinc, and gold and alloys thereof, metal oxides such as zinc oxide, indium oxide, indium thin oxide (ITO), and indium zinc oxide (IZO); combinations of metals and oxides such as ZnO:Al and $SnO_2$:Sb; and conductive polymers such as poly(3-methylthiophene), poly[3,4-(ethylene-1,2-dioxy)thiophene](PEDT), polypyrrole, and polyaniline.

As the cathode material, a material having a low work function is generally preferred for easy injection of electrons into the organic layers. Specific examples of suitable cathode materials include, but are not limited to: metals such as magnesium, calcium, sodium, potassium, titanium, indium, yttrium, lithium, gadolinium, aluminum, silver, tin, and lead and alloys thereof, and multilayer structure materials such as LiF/Al and $LiO_2$/Al.

The hole injecting material is preferably a material that may receive holes injected from the anode at low voltage. The highest occupied molecular orbital (HOMO) of the hole injecting material is preferably between the work function of the anode material and the HOMO of the adjacent organic layer. Specific examples of hole injecting materials include, but are not limited to, metal porphyrin, oligothiophene, arylamine-based organic materials, hexanitrile hexaazatriphenylene, quinacridone-based organic materials, perylene-based organic materials, anthraquinone, polyaniline, and polythiophene-based conductive polymers.

The hole transport material is a material that may receive holes transported from the anode or the hole injecting layer and may transfer the holes to the light emitting layer. A material with high hole mobility is suitable. Specific examples thereof include arylamine-based organic materials, conductive polymers, and block copolymers consisting of conjugated and non-conjugated segments. The use of the organic light emitting compound according to an embodiment of the present invention ensures further improved low-voltage driving characteristics, high luminous efficiency, and life characteristics of the device.

The light emitting material is a material that may receive and recombine holes from the hole transport layer and electrons from the electron transport layer to emit light in the visible ray area. A material with high quantum efficiency for fluorescence and phosphorescence is preferred. Specific examples thereof include, but are not limited to, 8-hydroxyquinoline aluminum complex ($Alq_3$), carbazole-based compounds, dimerized styryl compounds, BAlq, 10-hydroxybenzoquinoline-metal compounds, benzoxazole-based compounds, benzthiazole-based compounds, and benzimidazole-based compounds, poly(p-phenylenevinylene) (PPV)-based polymers, spiro compounds, polyfluorene, and rubrene.

The electron transport material is a material that may receive electrons injected from the cathode and may transfer the electrons to the light emitting layer. A material with high electron mobility is suitable. Specific examples thereof include, but are not limited to, 8-hydroxyquinoline Al complex, $Alq_3$ complexes, organic radical compounds, hydroxyflavone-metal complexes.

The organic light emitting device according to an embodiment of the present invention may be of a top emission, bottom emission or dual emission type according to the materials used.

In addition, the organic light emitting compound according to an embodiment of the present invention may perform its function even in organic electronic devices, including organic solar cells, organic photoconductors, and organic transistors, based on a similar principle to that applied to the organic light emitting device.

Mode for Carrying Out Invention

Hereinafter, the present invention will be explained in more detail with reference to the preferred examples. However, these examples are provided for illustrative purposes and do not serve to limit the scope of the invention. It will be obvious to those skilled in the art that various modifications and changes are possible without departing from the scope and technical spirit of the present invention.

Synthesis Example 1: Synthesis of Compound 1

(1) Preparative Example 1: Synthesis of Intermediate 1-1

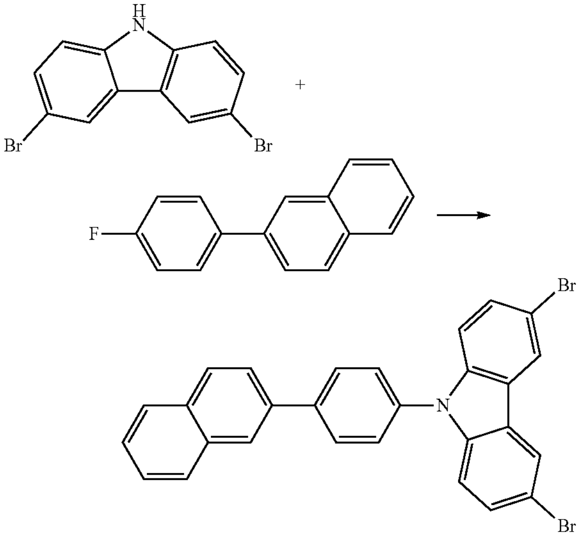

1-1

DMF 500 mL was added to 3,6-Dibromocarbazole (10 g, 0.031 mol), 2-(4-fluorophenyl)naphthalene (8.2 g, 0.037 mol), cesium carbonate (15 g, 0.046 mol). The mixture was refluxed with stirring at 150° C. for 15 hours. After completion of the reaction, the reaction mixture was extracted and purified by column chromatography to afford 16.8 g (yield 70.8%) of Intermediate 1-1.

(2) Preparative Example 2: Synthesis of Compound 1

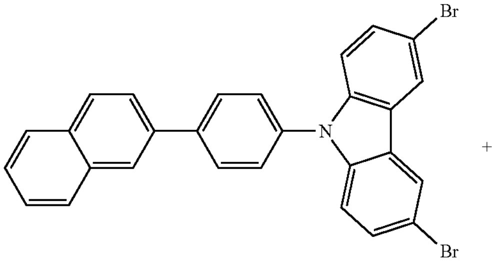

1-1

-continued

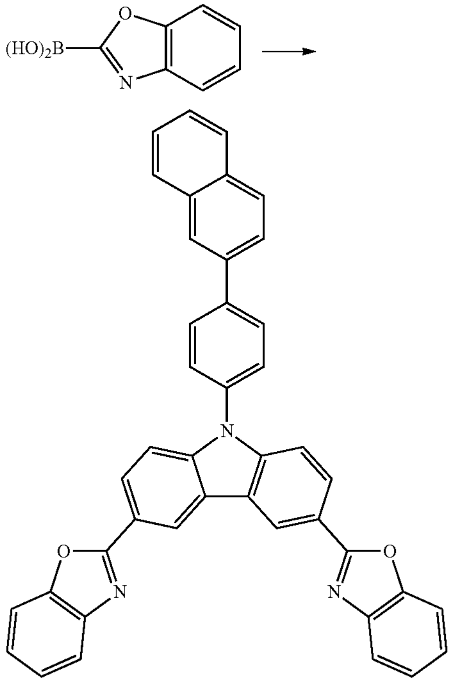

1

Intermediate 1-1 (10 g, 0.019 mol), benzo[d]oxazol-2-ylboronic acid (7.42 g, 0.046 mol), potassium carbonate (13.1 g, 0.095 mol), $Pd(PPh_3)_4$ (1.10 g, 0.001 mol), toluene 100 mL, $H_2O$ 30 mL, and Ethanol 30 mL were added, and then were refluxed with stirring at 95° C. for 6 hours. After completion of the reaction, the reaction mixture was extracted and purified by column chromatography to afford 7.5 g (yield 65.5%) of Compound 1.

LC/MS: m/z=603[$(M)^+$]

Synthesis Example 2: Synthesis of Compound 7

(1) Preparative Example 1: Synthesis of Compound 7

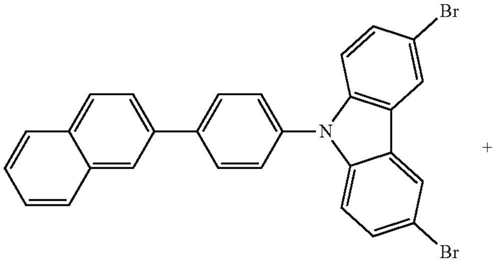

1-1

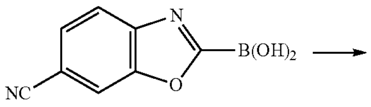

-continued

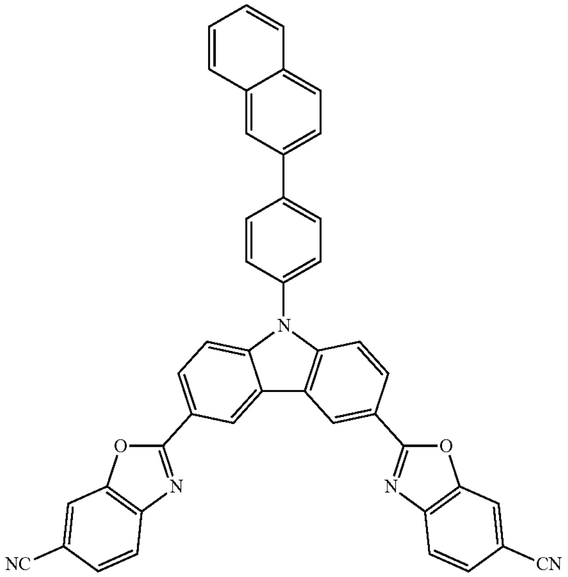

7

Intermediate 1-1 (10 g, 0.019 mol), 6-cyanobenzo[d]oxazol-2-ylboronic acid (8.56 g, 0.046 mol), potassium carbonate (13.1 g, 0.095 mol), $Pd(PPh_3)_4$ (1.10 g, 0.001 mol), toluene 100 mL, $H_2O$ 30 mL, and Ethanol 30 mL were added, and then were refluxed with stirring at 95° C. for 6 hours. After completion of the reaction, the reaction mixture was extracted and purified by column chromatography to afford 8.1 g (yield 65.3%) of Compound 7.

LC/MS: m/z=653[$(M)^+$]

Synthesis Example 3: Synthesis of Compound 16

(1) Preparative Example 1: Synthesis of Intermediate 16-1

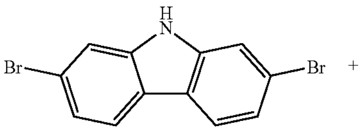

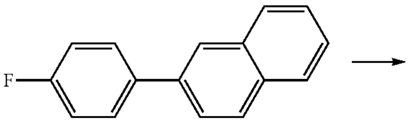

-continued

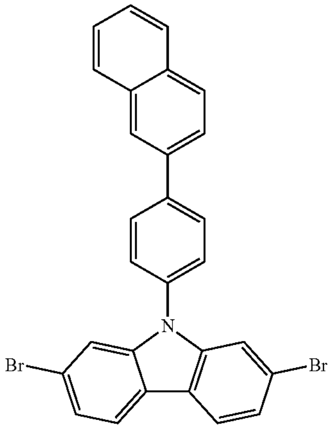

16-1

DMF 500 mL was added to 2,7-Dibromo-9H-carbazole (10 g, 0.031 mol), 2-(4-fluorophenyl)naphthalene (17.5 g, 0.037 mol), cesium carbonate (15 g, 0.046 mol). The mixture was refluxed with stirring at 150° C. for 12 hours. After completion of the reaction, the reaction mixture was extracted and purified by column chromatography to afford 16.8 g (yield 70.8%) of Intermediate 16-1.

(2) Preparative Example 2: Synthesis of Compound 16

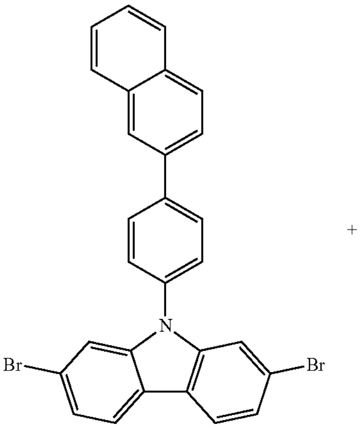

16-1

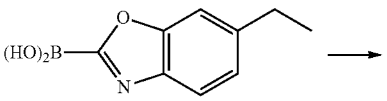

-continued

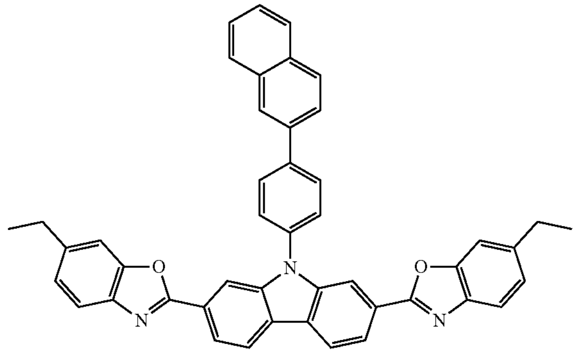

16

DMF 500 mL was added to Intermediate 16-1 (10 g, 0.019 mol), 6-ethylbenzo[d]oxazol-2-ylboronic acid (8.7 g, 0.046 mol), and cesium carbonate (13.1 g, 0.095 mol). The mixture was refluxed with stirring at 150° C. for 12 hours. After completion of the reaction, the reaction mixture was extracted and purified by column chromatography to afford 8.7 g (yield 69.5%) of Compound 16.

LC/MS: m/z=659[(M)$^+$]

Synthesis Example 4: Synthesis of Compound 27

(1) Preparative Example 1: Synthesis of Compound 27

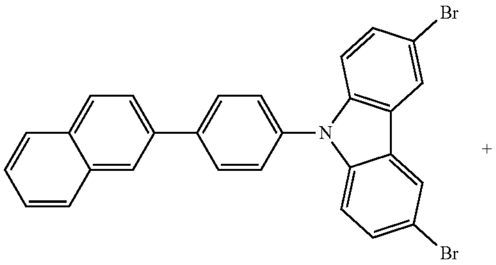

1-1

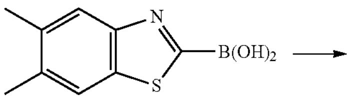

-continued

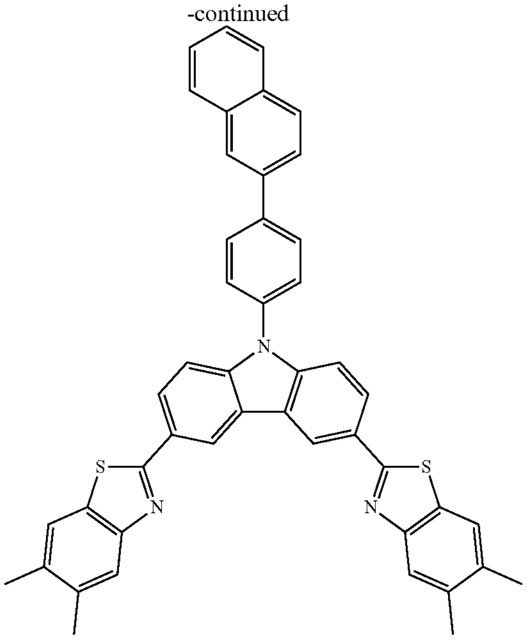

27

Intermediate 1-1 (10 g, 0.019 mol), 5,6-dimethylbenzo[d]thiazol-2-ylboronic acid (9.4 g, 0.046 mol), potassium carbonate (13.1 g, 0.095 mol), $Pd(PPh_3)_4$ (1.10 g, 0.001 mol), toluene 100 mL, $H_2O$ 30 mL, and Ethanol 30 mL were added, and then were refluxed with stirring at 95° C. for 6 hours. After completion of the reaction, the reaction mixture was extracted and purified by column chromatography to afford 8.9 g (yield 67.8%) of Compound 27.

LC/MS: m/z=691[(M)$^+$]

Synthesis Example 5: Synthesis of Compound 38

(1) Preparative Example 1: Synthesis of Compound 38

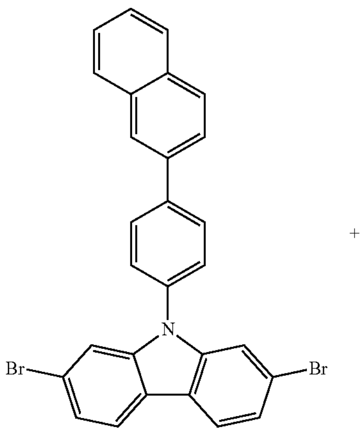

16-1

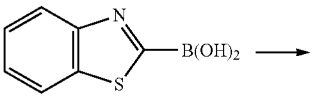

-continued

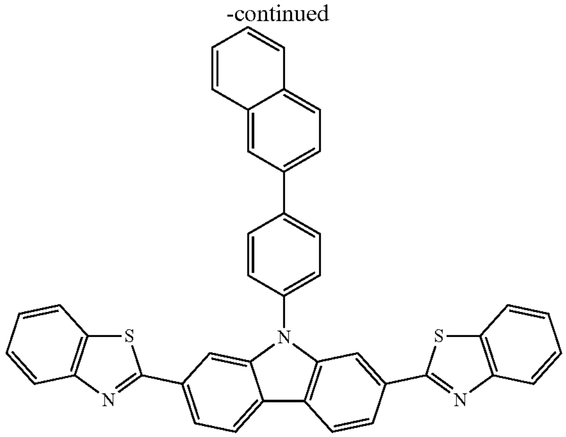

38

Intermediate 16-1 (10 g, 0.019 mol), benzo[d]thiazol-2-ylboronic acid (8.15 g, 0.046 mol), potassium carbonate (13.1 g, 0.095 mol), $Pd(PPh_3)_4$ (1.10 g, 0.001 mol), toluene 100 mL, $H_2O$ 30 mL, Ethanol 30 mL were added, and then were refluxed with stirring at 95° C. for 6 hours. After completion of the reaction, the reaction mixture was extracted and purified by column chromatography to afford 8.4 g (yield 69.7%) of Compound 38.

LC/MS: m/z=635[$(M)^+$]

Synthesis Example 6: Synthesis of Compound 49

(1) Preparative Example 1: Synthesis of Compound 49

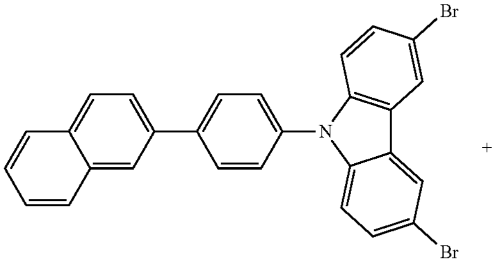

1-1

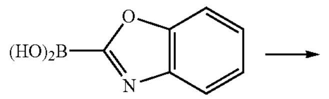

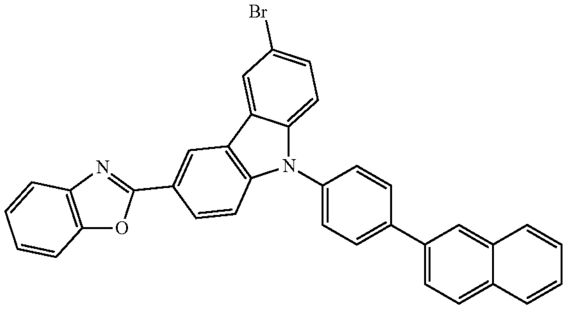

49-1

Intermediate 1-1 (10 g, 0.019 mol), benzo[d]oxazol-2-ylboronic acid (3.71 g, 0.023 mol), potassium carbonate (7.86 g, 0.057 mol), $Pd(PPh_3)_4$ (1.10 g, 0.001 mol), toluene 100 mL, $H_2O$ 30 mL, and Ethanol 30 mL were added, and then were refluxed with stirring at 95° C. for 6 hours. After completion of the reaction, the reaction mixture was extracted and purified by column chromatography to afford 7.3 g (yield 68.1%) of Intermediate 49-1.

(2) Preparative Example 2: Synthesis of Compound 49

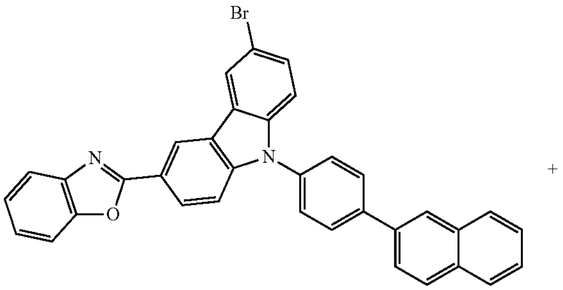

49-1

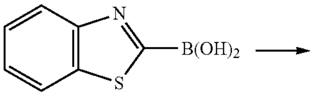

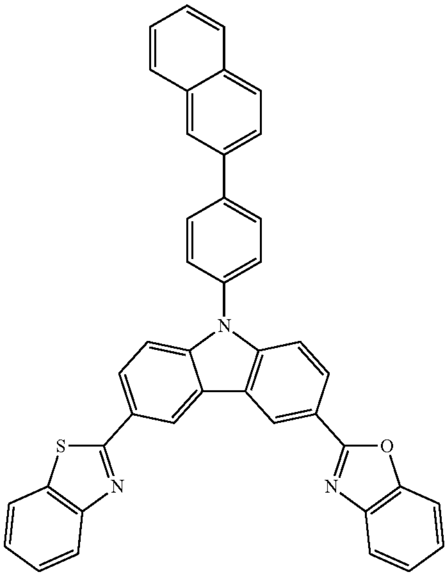

49

Intermediate 49-1 (10 g, 0.018 mol), benzo[d]thiazol-2-ylboronic acid (3.8 g, 0.021 mol), potassium carbonate (7.33 g, 0.053 mol), $Pd(PPh_3)_4$ (1.02 g, 0.001 mol), toluene 100 mL, $H_2O$ 30 mL, and Ethanol 30 mL were added, and then were refluxed with stirring at 95° C. for 6 hours. After completion of the reaction, the reaction mixture was extracted and purified by column chromatography to afford 8.1 g (yield 73.9%) of Intermediate 49.

LC/MS: m/z=619[$(M)^+$]

Experimental Example 1: Optical Characteristic of Compound According to Embodiment of Present Invention In the Experimental Example according to an embodiment of the present invention, a glass substrate having a size of 25 mm×25 mm was washed. Then, the glass substrate was mounted to a vacuum chamber, and when a base pressure is $1\times10^{-6}$ torr or larger, an optical characteristic was measured by depositing each of a compound according to an embodiment of the present invention and a comparative compound on the glass substrate.

(1) Examples 1 to 8

A refractive index was measured by depositing each of Compounds 1, 3, 9, 26, 27, 38, 46, and 49 according to an embodiment of the present invention on the glass substrate by 100 nm.

Quartz Glass/Organic Material (100 nm)

(2) In Comparative Example 1, the optical characteristic was measured by fabricating the substrate in the same manner, except that CPI was used instead of the compound implemented in an embodiment of the present invention.

(3) A refractive index of the substrate fabricated as above was measured by using Ellipsometry (Elli-SE). The result values at the 450 nm reference wavelength are shown in [Table 1] below.

TABLE 1

| Examples & Comparative Example | Compounds | n (450 nm) |
|---|---|---|
| Example 1 | Formula 1 | 2.28 |
| Example 2 | Formula 3 | 2.25 |
| Example 3 | Formula 9 | 2.24 |
| Example 4 | Formula 26 | 2.29 |
| Example 5 | Formula 27 | 2.26 |
| Example 6 | Formula 38 | 2.23 |
| Example 7 | Formula 46 | 2.23 |
| Example 8 | Formula 49 | 2.26 |
| Comparative Example 1 | CP1 | 2.07 |

As can be seen from the results in Table 1 above, it was identified that the compound according to an embodiment of the present invention had a refractive index value of 2.20 or more at 450 nm. The compound according to an embodiment of the present invention has a higher refractive index than Comparative Example 1 and is more suitable as a material for the light efficiency improving layer. Thus, the device characteristic can be further improved when the compound according to an embodiment of the present invention is employed as a light efficiency improving layer.

Device Examples (Capping Layer)

In an example of the present invention, an Ag-containing ITO glass substrate having dimensions of 25 mm×25 mm×0.7 mm was used as an anode, patterned to have a light emitting area of 2 mm×2 mm, followed by cleaning. After the patterned ITO substrate was mounted in a vacuum chamber, organic materials and metals were deposited in the following structure on the substrate at a process pressure of $1\times10^{-6}$ torr or more.

Device Examples 9 to 16

Blue organic light emitting devices having the following device structure were fabricated employing the compounds implemented according to an embodiment of the present invention in the light efficiency improving layer. The luminescent properties including luminescent efficiencies were measured.

Ag:ITO/hole injecting layer (HAT-CN, 5 nm)/hole transport layer (α-NPB, 100 nm)/electron blocking layer (TCTA, 10 nm)/light emitting layer (20 nm)/electron transport layer (201:Liq, 30 nm)/LiF (1 nm)/Mg:Ag (15 nm)/light efficiency improving layer (70 nm)

On a glass substrate, HAT-CN was formed into a film to form a 5 nm thick hole injecting layer on an Ag-containing ITO transparent electrode. Thereafter, a 100 nm thick hole transport layer was formed into a film using α-NPB. A 10 nm thick electron blocking layer was formed into a film using TCTA. In addition, a 20 nm thick light emitting layer was co-deposited using BH1 as a host compound and BD1 as a dopant compound. Additionally, a 30 nm thick electron transport layer (doped with Liq 50% of the following [201] compound) was formed into a film and a 1 nm thick LiF layer was formed into a film. Subsequently, a 15 nm thick Mg:Ag layer was formed into a film in a ratio of 1:9. In addition, as a light efficiency improving layer (capping layer) compound, compounds 1, 3, 9, 26, 27, 38, 46, and 49 implemented in an embodiment of the present invention were formed into a film to a thickness of 70 nm to fabricate an organic light emitting device.

Device Comparative Example 1

An organic light emitting device for Device Comparative Example 1 was fabricated in the same manner, except that CP1 was used instead of the compound of an embodiment of the present invention as the light efficiency improving layer compound in the device structures of Examples 9 to 16.

Device Comparative Example 2

An organic light emitting device for Device Comparative Example 2 was fabricated in the same manner, except that the light efficiency improving layer was not used in the device structures of Examples 9 to 16.

Device Comparative Example 3

An organic light emitting device for Device Comparative Example 3 was fabricated in the same manner, except that $Alq_3$ was used instead of the compound of an embodiment of the present invention as the light efficiency improving layer compound in the device structures of Examples 9 to 16.

Experimental Example 2: Luminescent Properties of Device Examples 9 to 16

The driving voltages, current efficiencies, and color coordinates of the organic light emitting devices fabricated in the above Examples were measured at 1,000 nits using a source meter (Model 237, Keithley) and a spectroradiometer (PR-650, Photo Research). The result values are shown in Table 2 below.

TABLE 2

| Examples & Comparative Examples | Light efficiency improving layer | V | cd/A | CIEx | CIEy |
|---|---|---|---|---|---|
| Example 9 | Formula 1 | 3.6 | 8.8 | 0.140 | 0.042 |
| Example 10 | Formula 3 | 3.7 | 8.6 | 0.141 | 0.042 |
| Example 11 | Formula 9 | 3.7 | 8.5 | 0.142 | 0.041 |
| Example 12 | Formula 26 | 3.6 | 8.7 | 0.142 | 0.040 |
| Example 13 | Formula 27 | 3.6 | 8.9 | 0.140 | 0.040 |

TABLE 2-continued

| Examples & Comparative Examples | Light efficiency improving layer | V | cd/A | CIEx | CIEy |
|---|---|---|---|---|---|
| Example 14 | Formula 38 | 3.7 | 8.3 | 0.142 | 0.041 |
| Example 15 | Formula 46 | 3.7 | 8.3 | 0.141 | 0.040 |
| Example 16 | Formula 49 | 3.6 | 8.7 | 0.142 | 0.041 |
| Comparative Example 1 | CP1 | 3.9 | 7.8 | 0.148 | 0.055 |
| Comparative Example 2 | Not used | 4.5 | 7.0 | 0.151 | 0.140 |
| Comparative Example 3 | $Alq_3$ | 4.3 | 7.8 | 0.149 | 0.057 |

As can be seen from the results in Table 2, it was identified that when the compound according to an embodiment of the present invention having a high refractive index value was applied to a device as a light efficiency improving layer, the devices were driven at lower voltages and had improved current efficiencies than the conventional devices (Comparative Examples 1, 2 and 3).

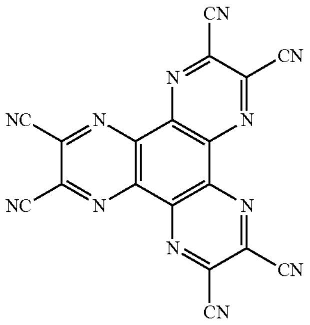

[HAT-CN]

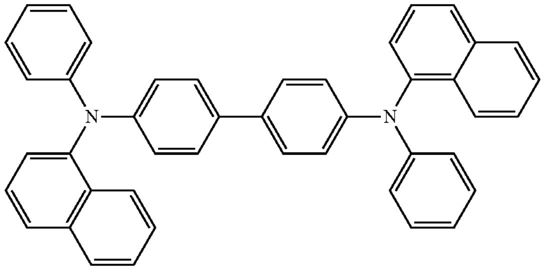

[α-NPB]

[BH1]

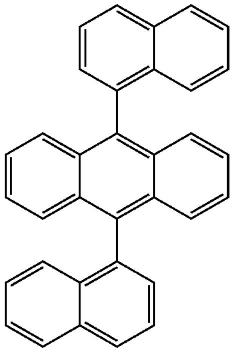

-continued

[BD1]

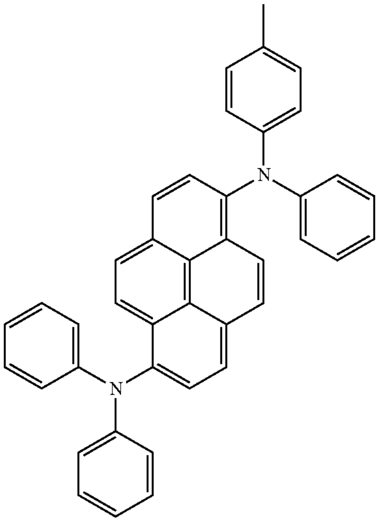

[201]

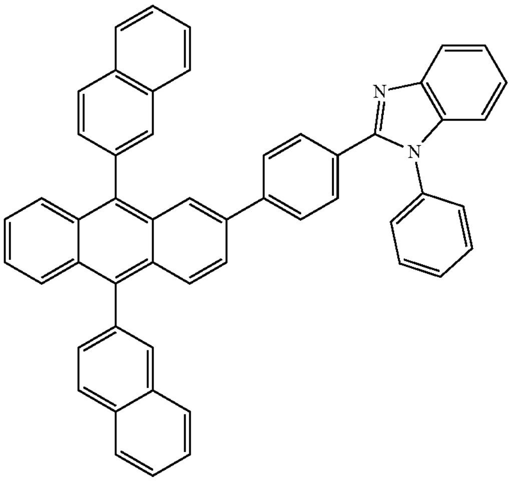

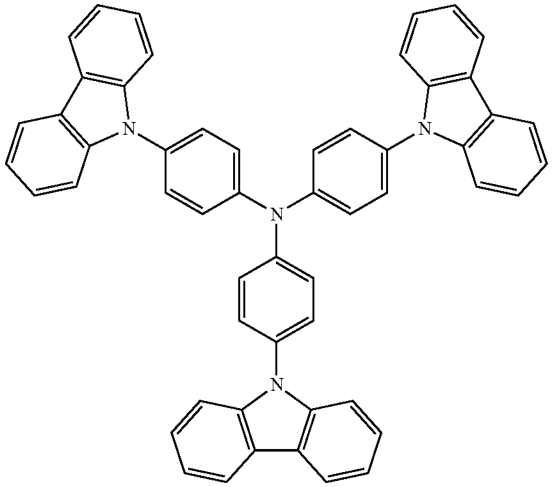

[TCTA]

-continued

[CP1]

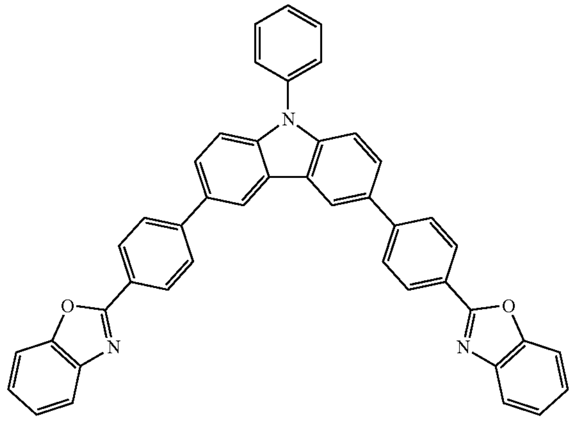

INDUSTRIAL APPLICABILITY

When an organic light emitting compound according to an embodiment of the present invention is employed as a material for a light efficiency improving layer provided in an organic light emitting device, it is possible to achieve luminescent properties such as low-voltage driving of the device and excellent luminous efficiency, and thus can be usefully used in various display devices.

The invention claimed is:

1. An organic light emitting compound represented by Formula I below:

[Formula I]

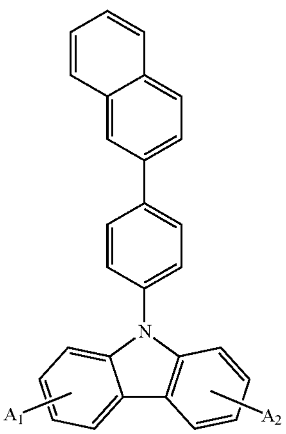

wherein, $A_1$ to $A_2$ are the same as or different from each other, and are each independently any one selected from among those represented by Structural Formula 2 to Structural Formula 6 below:

[Structural Formula 2]

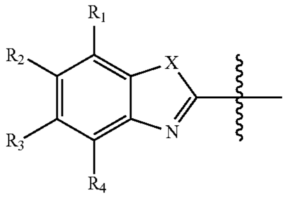

-continued

[Structural Formula 3]

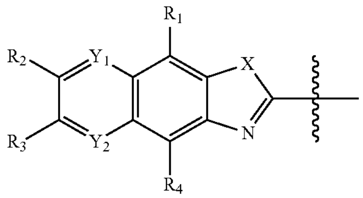

[Structural Formula 4]

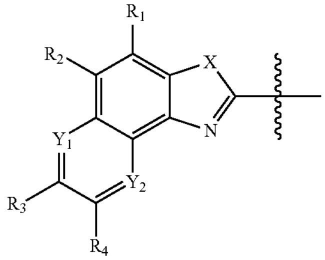

[Structural Formula 5]

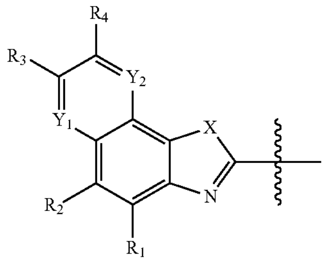

[Structural Formula 6]

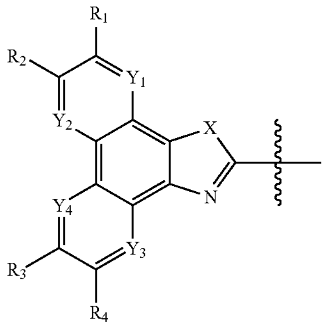

wherein,

X is O or S, $Y_1$ to $Y_4$ are the same as or different from each other, and each independently represents N or $CR_5$, and $R_1$ to $R_4$ and the $R_5$ are the same as or different from each other, and are each independently selected from hydrogen, deuterium, a halogen group, a cyano group, a substituted or unsubstituted C1 to C20 alkyl group, a substituted or unsubstituted C2 to C20 alkenyl group, a substituted or unsubstituted C3 to C20 cycloalkyl group, a substituted or unsubstituted C1 to C20 alkoxy group, a substituted or unsubstituted C1 to C20 halogenated alkyl group, a substituted or unsubstituted C1 to C20 halogenated alkoxy group, a substituted or unsubstituted C6 to C30 aryl group, and a substituted or unsubstituted C3 to C30 heteroaryl group.

2. The compound of claim 1, wherein the term "substituted" or "unsubstituted" in the definition of the $R_1$ to $R_5$ indicates substitution with one or more substituents selected from the group consisting of hydrogen, deuterium, a halogen group, a cyano group, a nitro group, a hydroxyl group, a silyl group, an alkyl group, a cycloalkyl group, an alkoxy group, an alkenyl group, an aryl group, and a heterocyclic group, substitution with a substituent to which two or more of the substituents are linked, or having no substituent.

3. The compound of claim 1, wherein the Formula I is selected from Compound 1 to Compound 56 below:

1

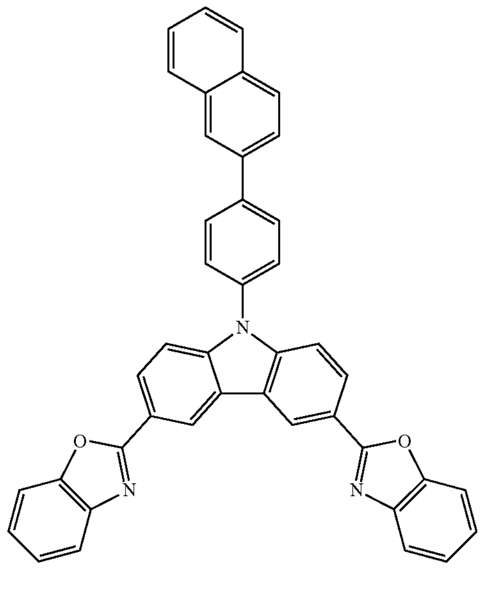

2

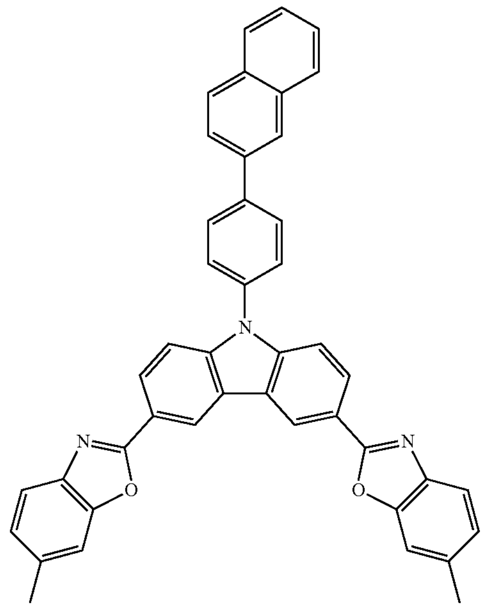

3

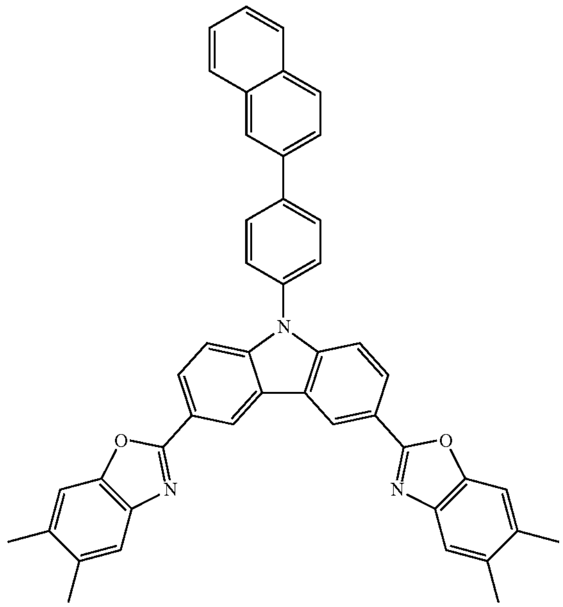

4

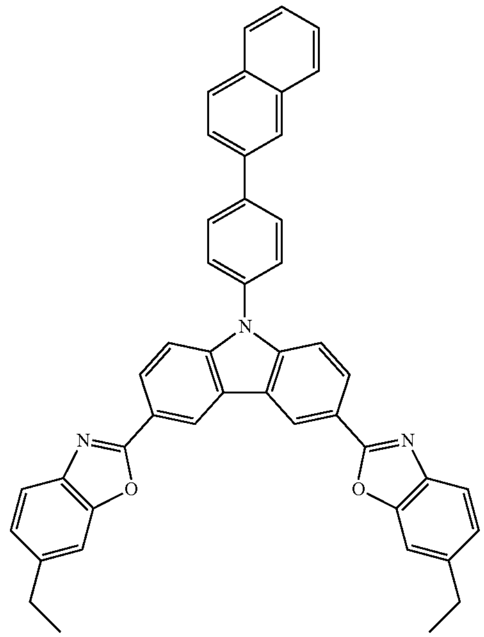

-continued
5
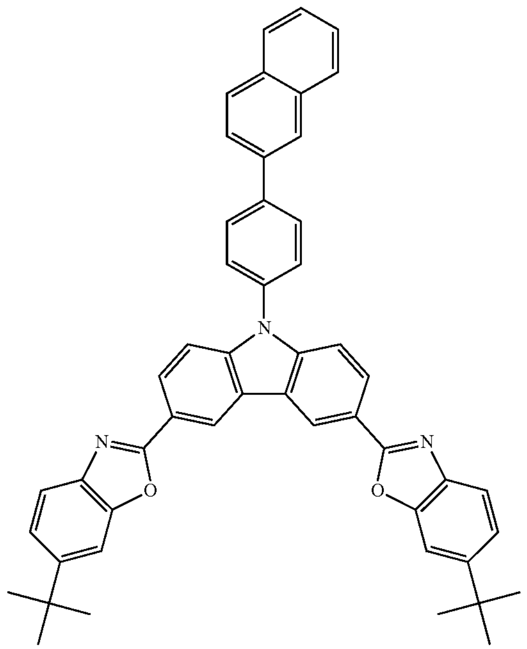
6
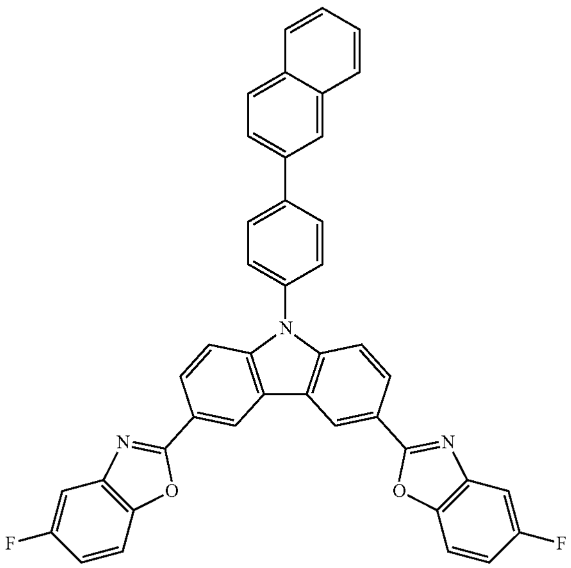
7
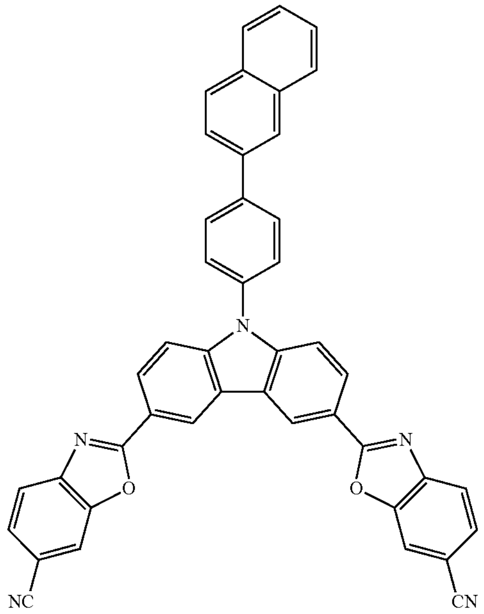
8
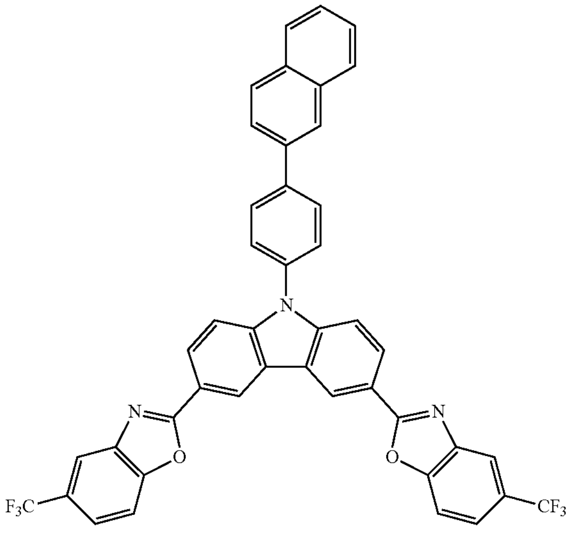

-continued
9
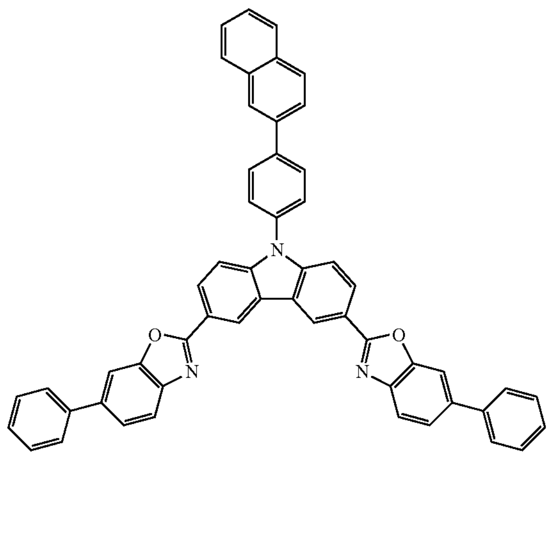
10
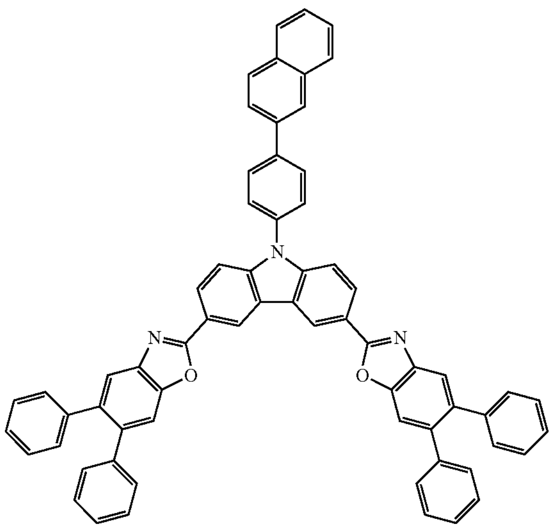
11
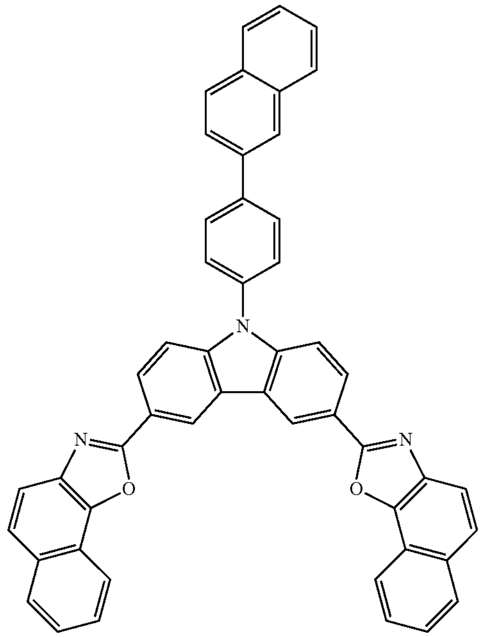
12
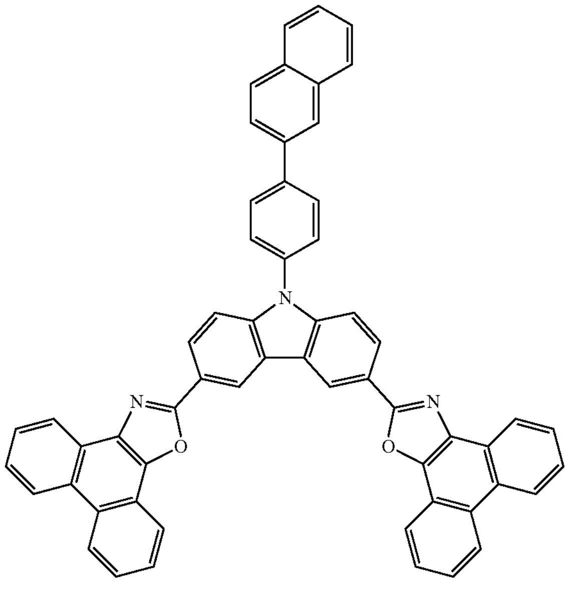

-continued
13
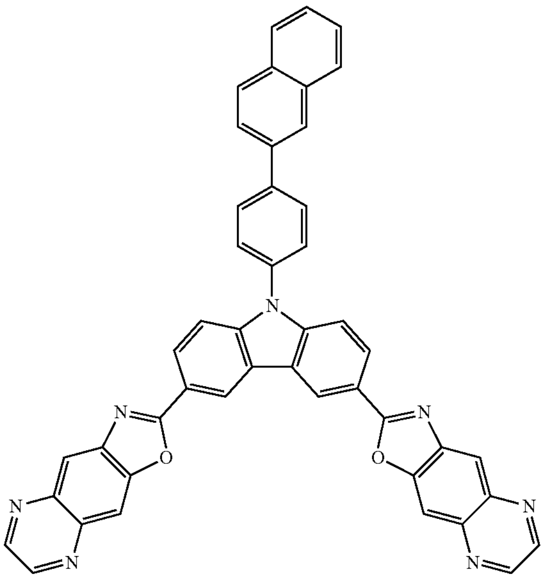
14
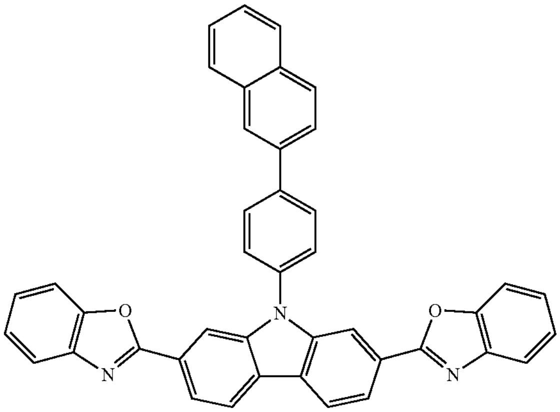
15
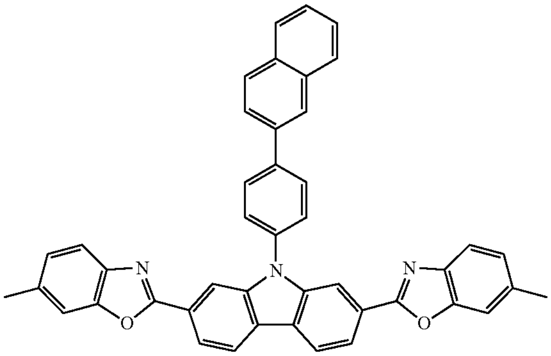
16
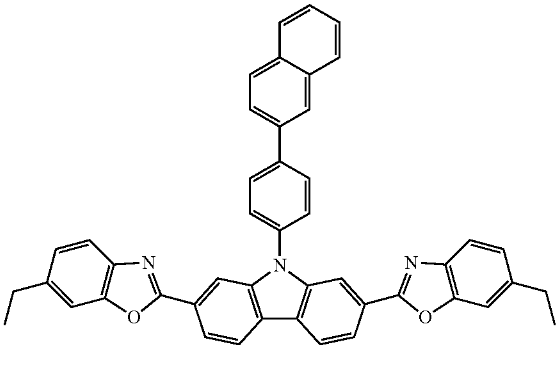
17
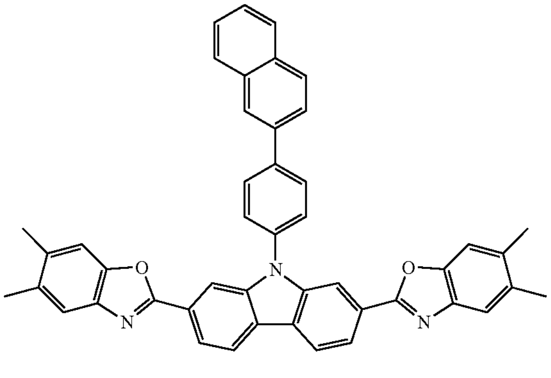
18
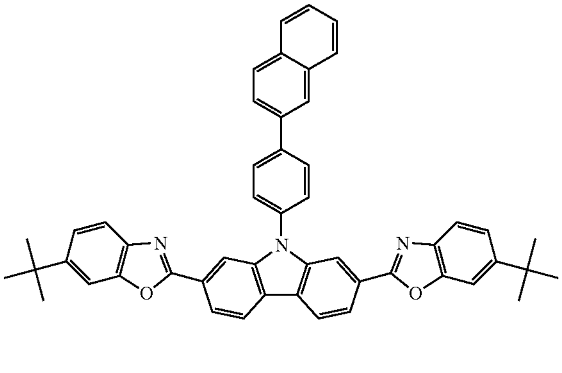

-continued
19
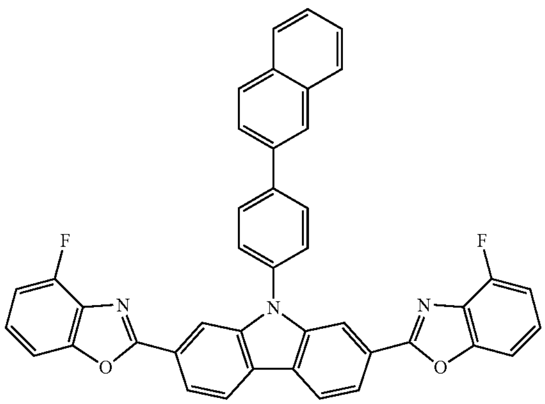
20
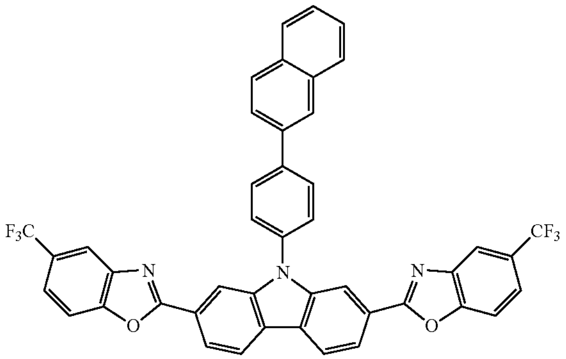
21
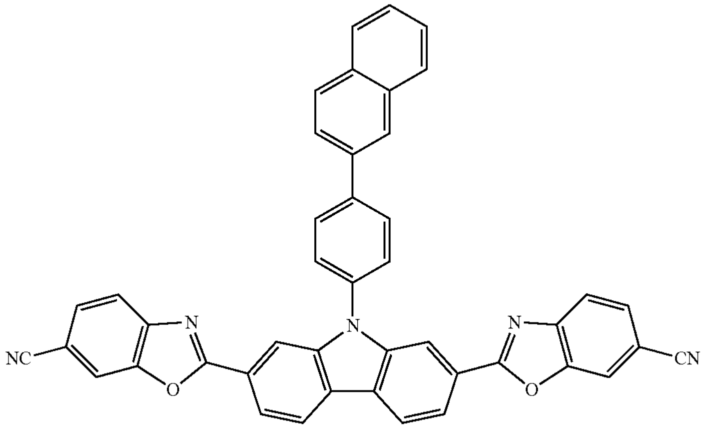
22
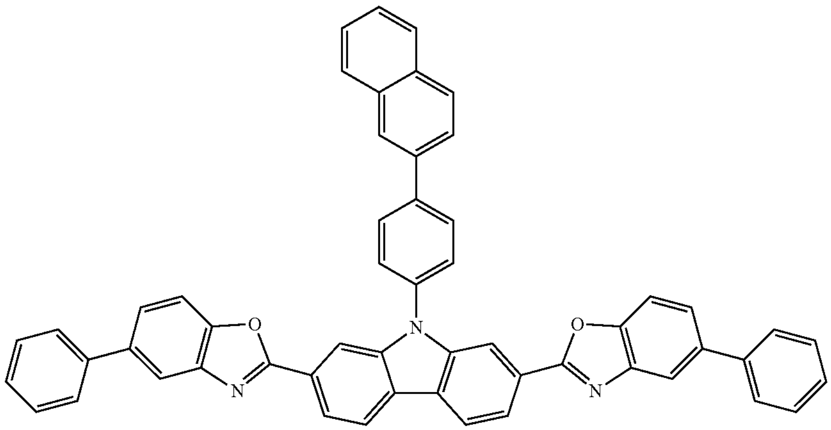

-continued
23
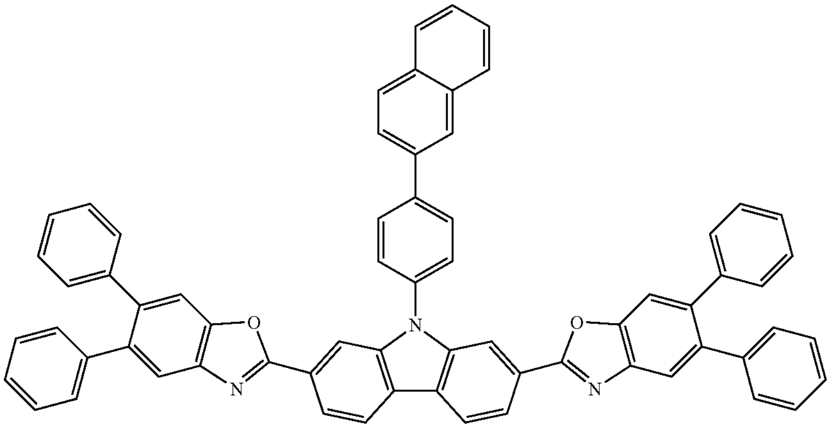
24
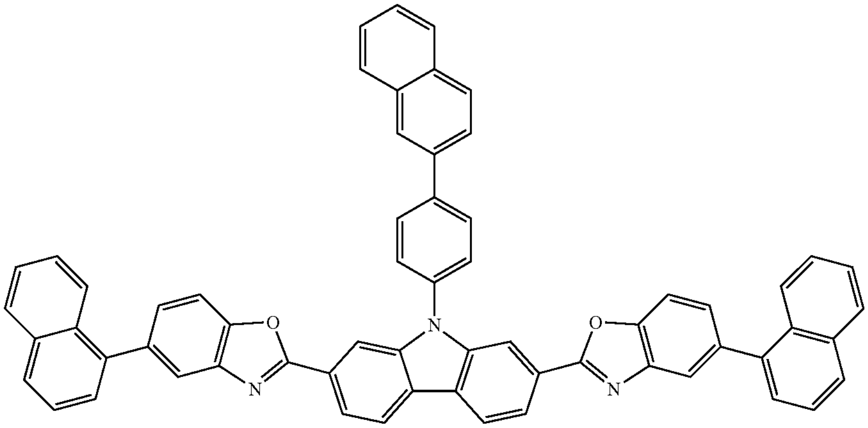
25
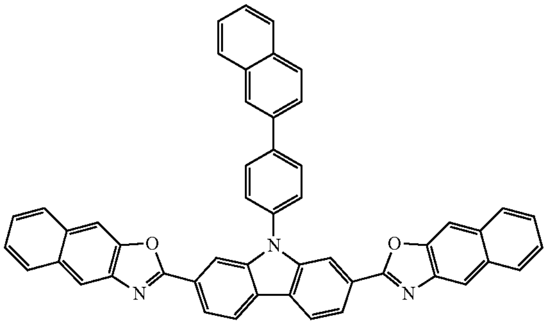
26
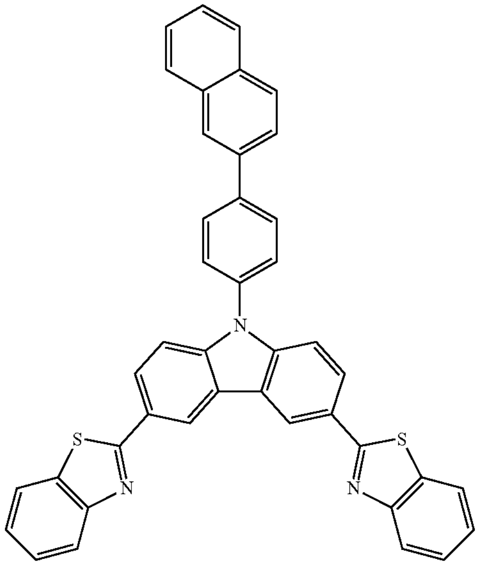

-continued
27
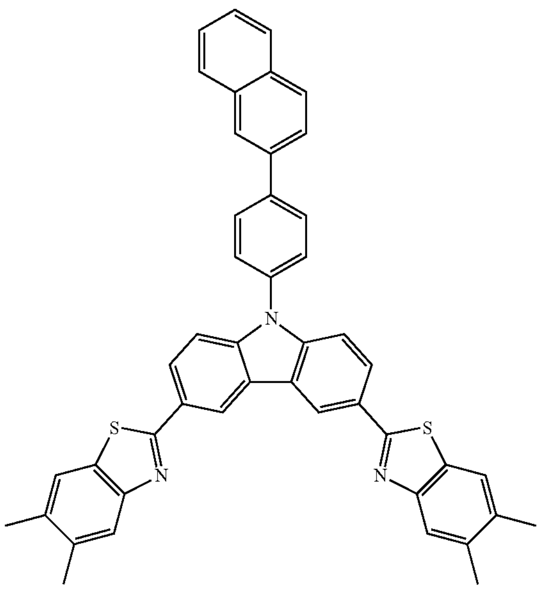
28
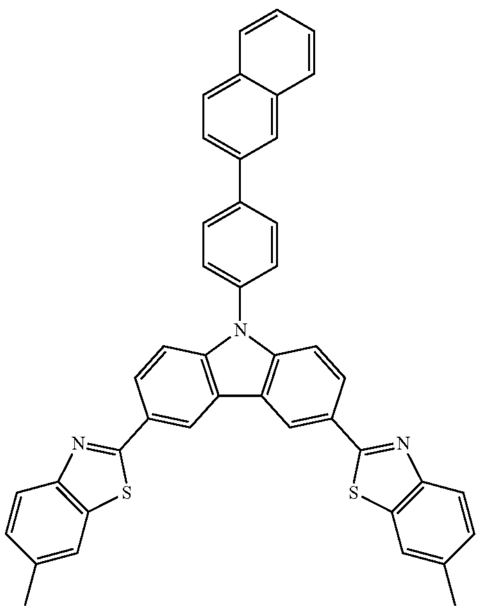
29
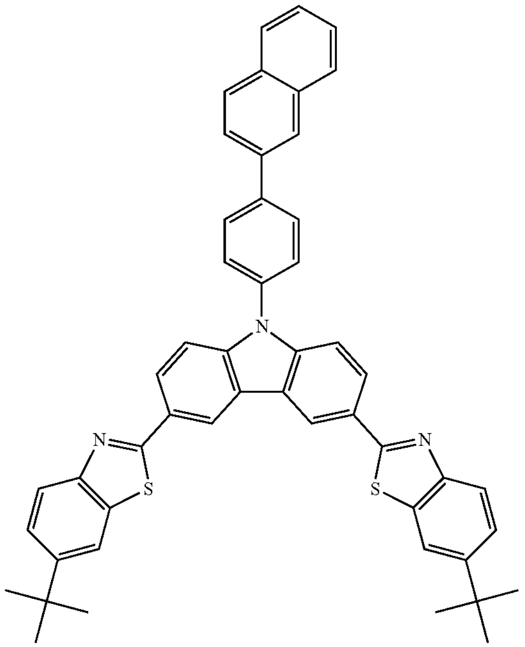
30
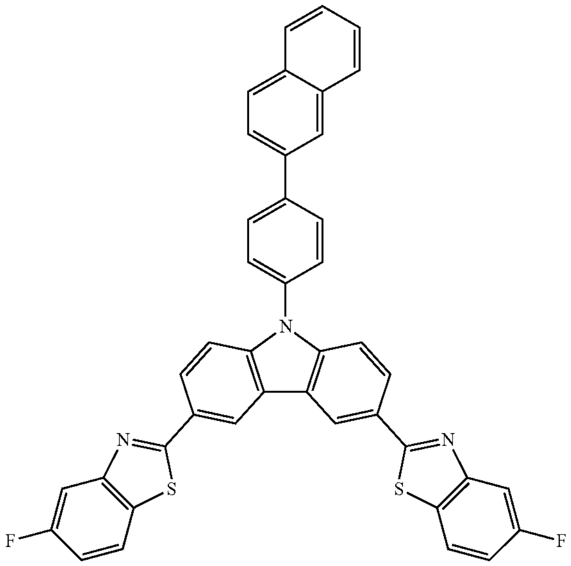

-continued
31
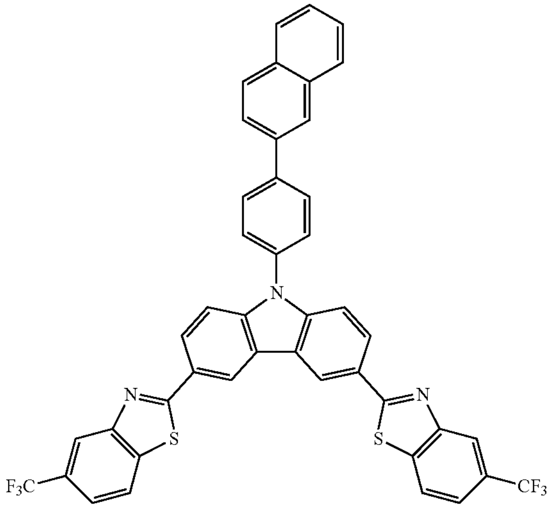
32
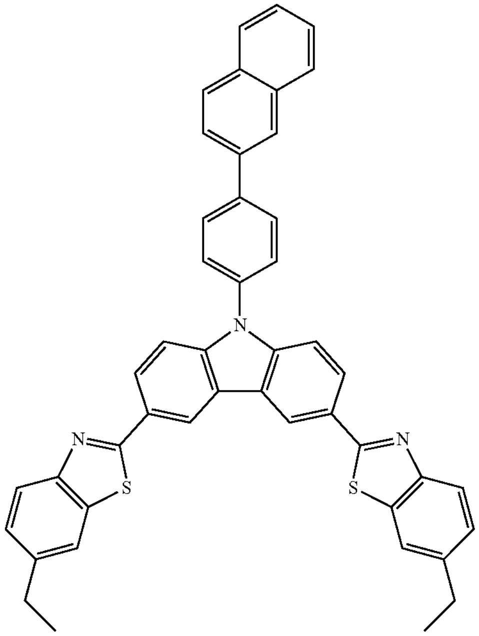
33
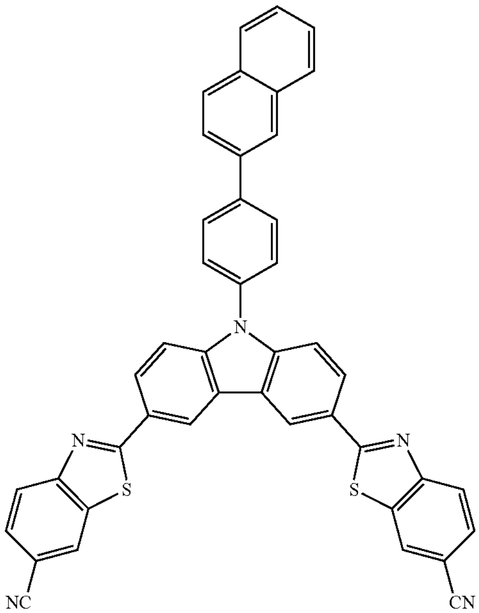
34
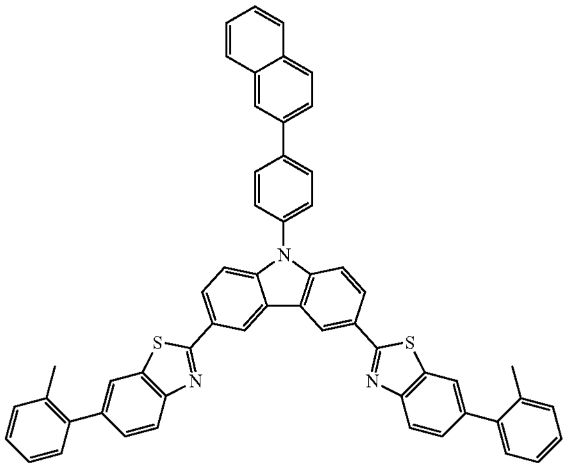

-continued
35
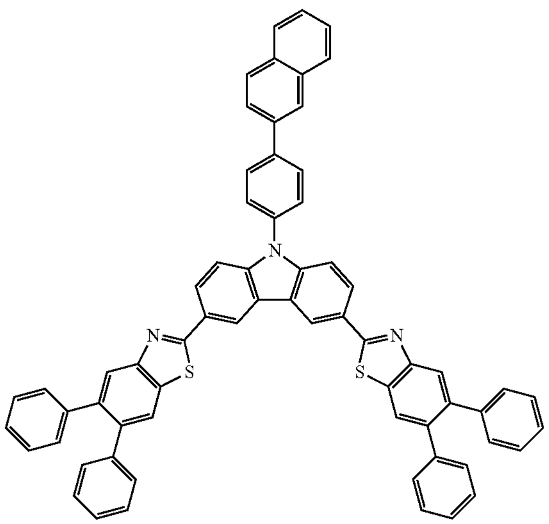
36
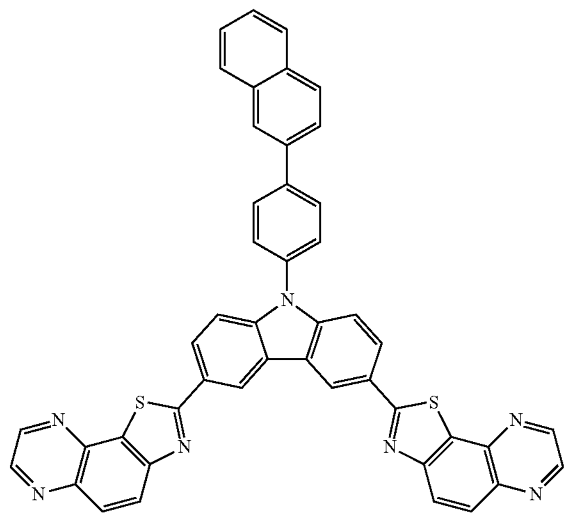
37
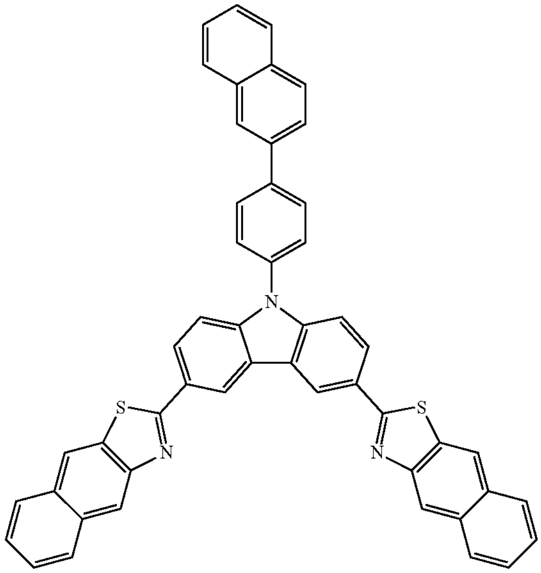
38
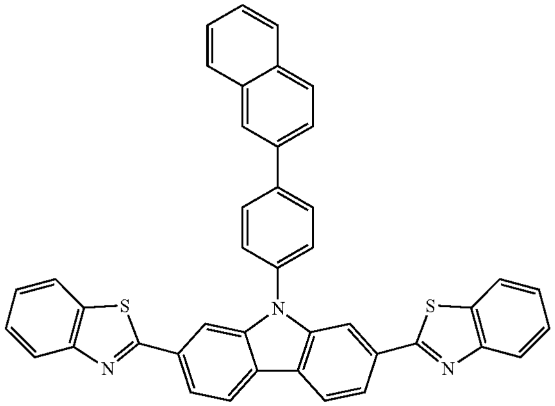
39
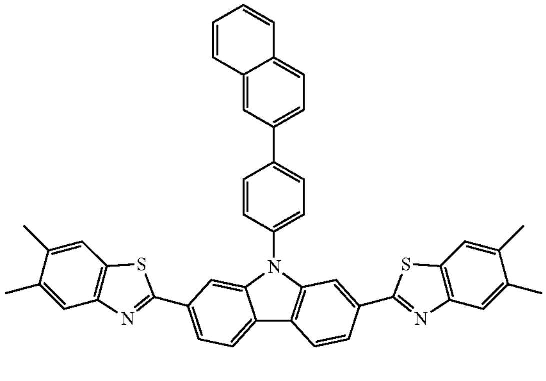
40
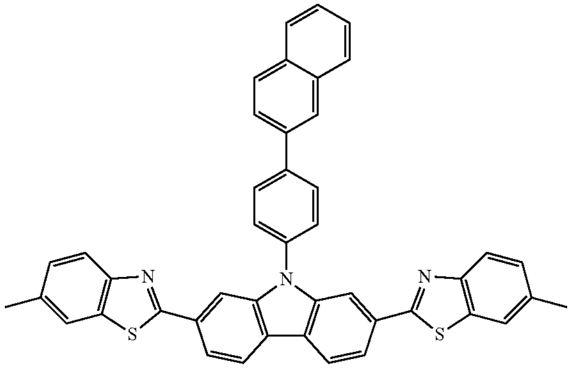

-continued
41
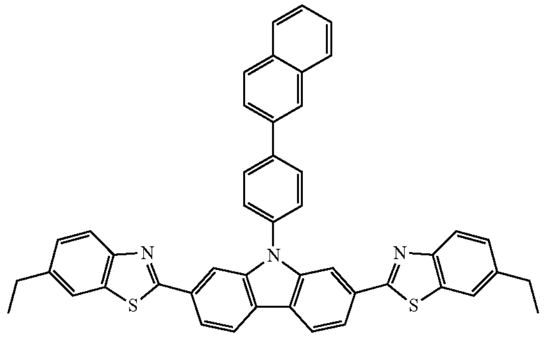
42
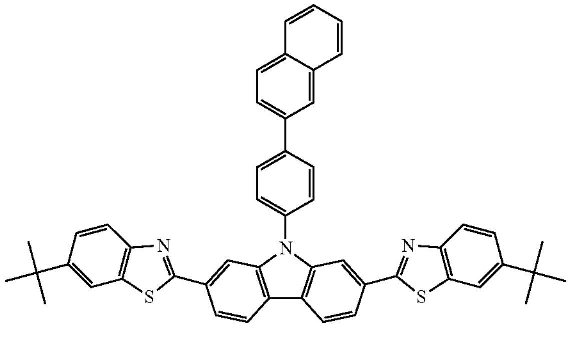
43
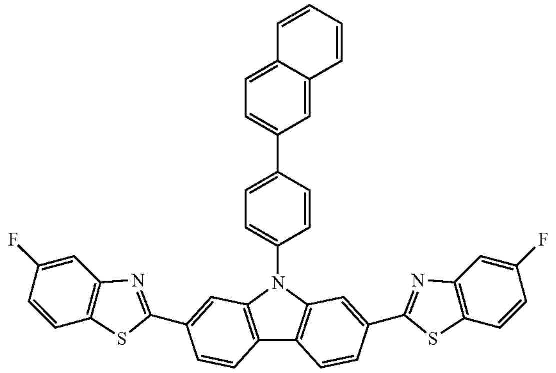
44
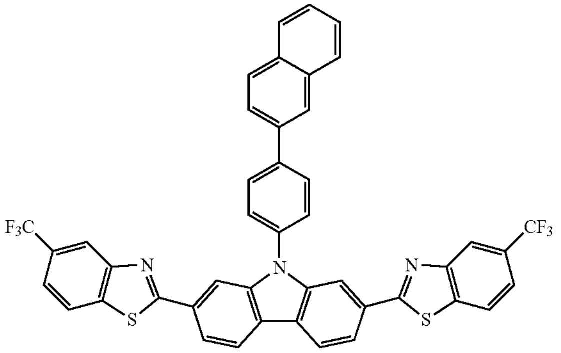
45
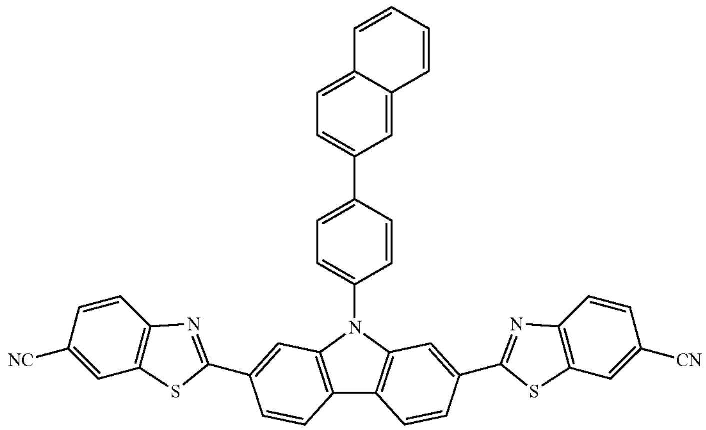
46
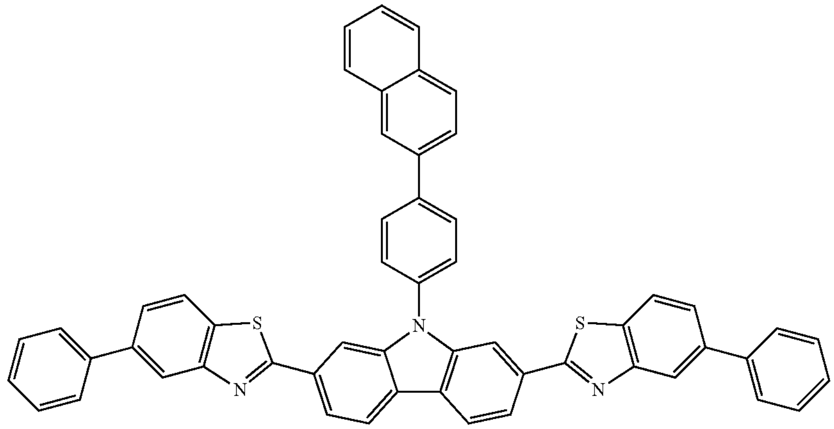

-continued
47
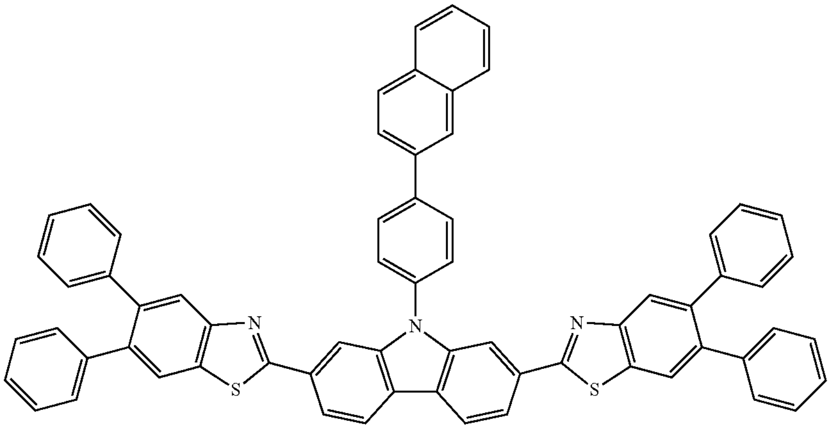
48
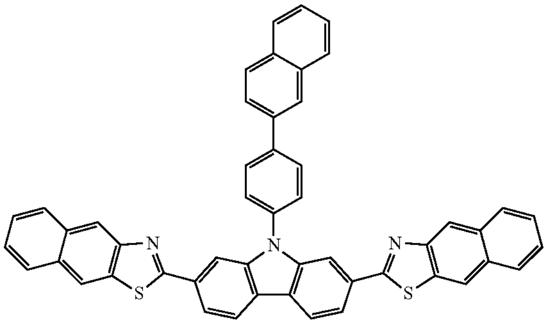
49
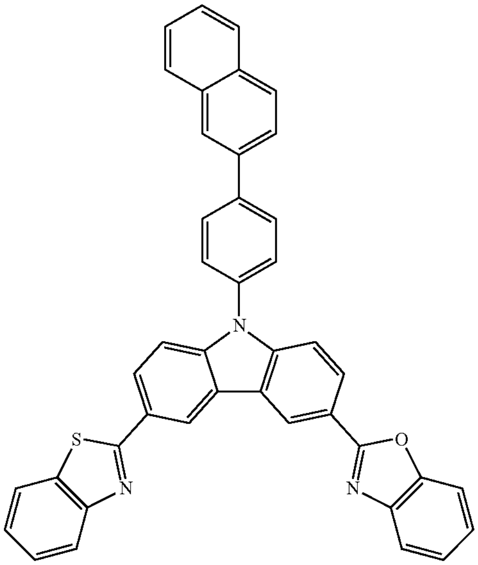
50
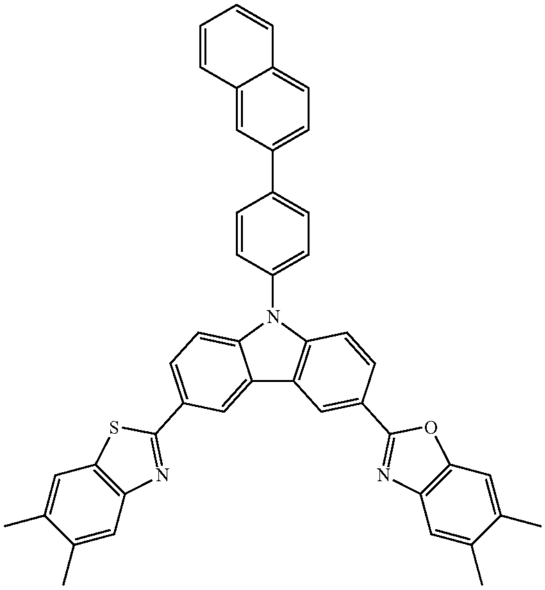
51
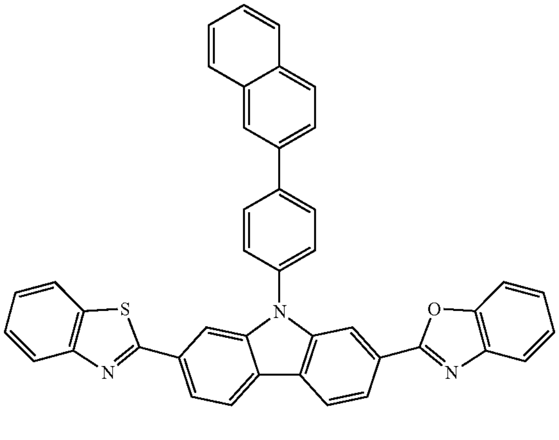

-continued

52

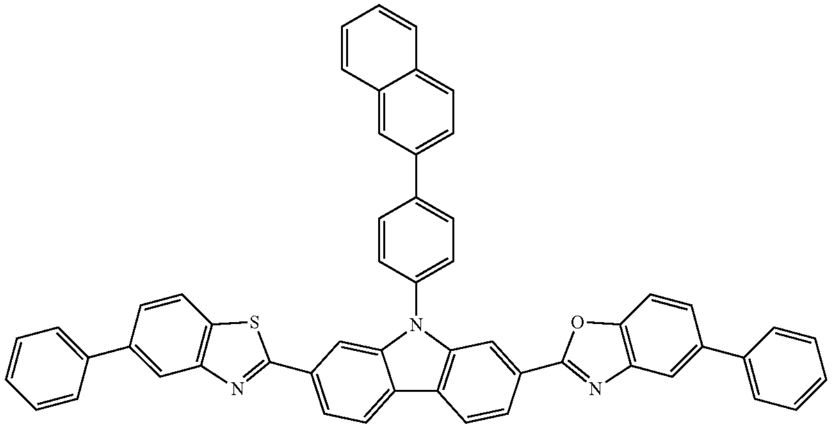

53

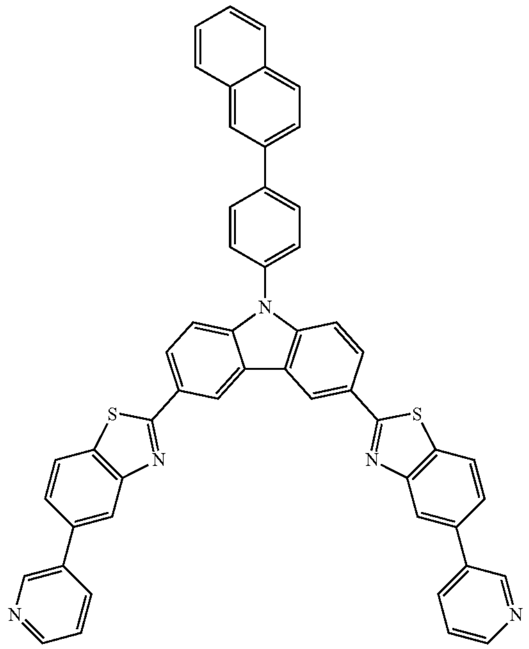

54

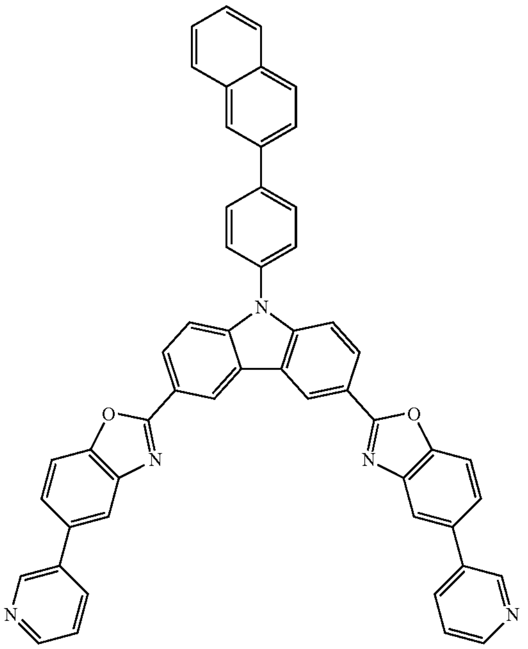

55

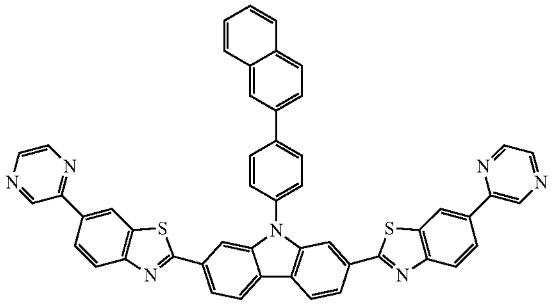

56

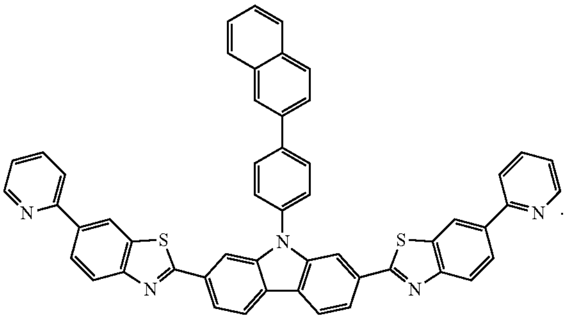

4. An organic light emitting device including a first electrode, a second electrode, and one or more organic layers arranged between the first and second electrodes, wherein the one or more organic layers include an organic light emitting compound represented by Formula I according to claim 1.

5. The device of claim 4, wherein:

the one or more organic layers include one or more layers selected from a hole injecting layer, a hole transport layer, a layer having functions of both hole injection and hole transport, an electron transport layer, an electron injecting layer, a layer having functions of both electron transport and electron injection, an electron blocking layer, a hole blocking layer, and a light emitting layer; and the one or more organic layers include an organic light emitting compound represented by the Formula I.

6. The device of claim 4, further including a light efficiency improving layer (capping layer) formed on at least one side opposite to the organic layer among upper or lower portions of the first electrode and the second electrode, wherein the light efficiency improving layer includes an organic light emitting compound represented by the Formula I.

7. The device of claim 6, wherein the light efficiency improving layer is formed on at least one of a lower portion of the first electrode or an upper portion of the second electrode.

8. The device of claim 6, wherein the light efficiency improving layer has a thickness of 50 to 150 nm, and has a refractive index value of 2.10 or more at a wavelength of 450 nm.

* * * * *